US011667929B2

(12) United States Patent
Cawood et al.

(10) Patent No.: US 11,667,929 B2
(45) Date of Patent: Jun. 6, 2023

(54) RETROVIRAL VECTORS

(71) Applicant: OXFORD GENETICS LIMITED, Oxford (GB)

(72) Inventors: Ryan Cawood, Oxford (GB); Tom Payne, Oxford (GB); Lucia Dunajova, Oxford (GB); Richard Parker-Manuel, Oxford (GB)

(73) Assignee: Oxford Genetics Limited, Oxford (GB)

( * ) Notice: Subject to any disclaimer, the term of this patent is extended or adjusted under 35 U.S.C. 154(b) by 520 days.

(21) Appl. No.: 16/647,697

(22) PCT Filed: Sep. 18, 2018

(86) PCT No.: PCT/GB2018/052656
§ 371 (c)(1),
(2) Date: Mar. 16, 2020

(87) PCT Pub. No.: WO2019/058108
PCT Pub. Date: Mar. 28, 2019

(65) Prior Publication Data
US 2020/0277629 A1 Sep. 3, 2020

(30) Foreign Application Priority Data

Sep. 19, 2017 (GB) .................................... 1715052

(51) Int. Cl.
| *A61K 35/17* | (2015.01) |
| *C12N 15/85* | (2006.01) |
| *C12N 5/10* | (2006.01) |
| *C12N 15/86* | (2006.01) |
| *C07K 14/005* | (2006.01) |
| *C07K 14/47* | (2006.01) |
| *C12N 5/071* | (2010.01) |
| *C12N 15/64* | (2006.01) |

(52) U.S. Cl.
CPC .......... *C12N 15/86* (2013.01); *C07K 14/4747* (2013.01); *C12N 5/0602* (2013.01); *C12N 15/64* (2013.01); *C12N 2740/16043* (2013.01)

(58) Field of Classification Search
CPC .... C07K 14/005; C07K 1/10; C12N 2510/00; C12N 2501/48; A61K 2039/5156
See application file for complete search history.

(56) References Cited

FOREIGN PATENT DOCUMENTS

| WO | 2006/089001 A2 | 8/2006 |
| WO | 2012028680 A1 | 3/2012 |
| WO | 2012028681 A1 | 3/2012 |
| WO | 2016/189326 A1 | 12/2016 |
| WO | 2017089307 A1 | 6/2017 |
| WO | 2017089308 A1 | 6/2017 |

OTHER PUBLICATIONS

Altschul, et al., "Gapped BLAST and PSI-BLAST: A New Generation of Protein Database Search Programs", Nucleic Acids Res., 1997, vol. 25(17), pp. 3389-3402.
Blanco, R., et al., "Cell Killing by HIV-1 Protease", The Journal of Biochemistry, Jan. 10, 2003, vol. 278(2), pp. 1086-1093.
Boussif, O., et al., "A Versatile Vector for Gene and Oligonucleotide Transfer Into Cells in Culture and in Vivo: Polyethylenimine", Proc. Natl. Acad. Sci. USA, Aug. 1, 1995, vol. 92(16), pp. 7297-7301.
Burns, J.C., et al., "Vesicular Stomatitis Virus G Glycoprotein Pseudotyped Retroviral Vectors: Concentration to Very High Titer and Efficient Gene Transfer Into Mammalian and Nonmammalian Cells", Proc. Natl. Acad. Sci., Sep. 1, 1993, vol. 90(17), pp. 8033-8037.
Coffin, J.M., et al., "Principles of Retroviral Vector Design", Retroviruses, 1997, Cold Spring Harbor (NY): Cold Spring Harbor Laboratory Press, Dec. 31, 1997, pp. 1-20.
Finkelstein, D., et al., "LDL Receptor and its Family Members Serve as the Cellular Receptors for Vesicular Stomatitis Virus", Proc. Natl. Acad. Sci. USA, Apr. 30, 2013, vol. 110(18), pp. 7306-7311.
Hoffman, M., et al., "Fusion-Active Glycoprotein G Mediates the Cytotoxicity of Vesicular Stomatitis Virus M Mutants Lacking Host Shut-Off Activity", J. Gen. Virol, Nov. 2010, vol. 91(Pt 11), pp. 2782-2793.
Ikeda, Y., et al., "Continuous High-Titer HIV-1 Vector Production", Nature Biotechnology, May 1, 2003, vol. 21(5), pp. 569-572.
Ma, B., et al., "PatternHunter: Faster and More Sensitive Homology Search", Bioinformatics, Mar. 2002, vol. 18(3), pp. 440-445.
Maurya, S.K., et al., "Retroviral Vectors and Gene Therapy: An Update", Indian Journal of Biotechnology, Oct. 1, 2009, vol. 8, pp. 349-357.
Sevier, C.S., et al., "Efficient Export of the Vesicular Stomatitis Virus G Protein From the Endoplasmic Reticulum Requires a Signal in the Cytoplasmic Tail That Includes Both Tyrosine-Based and Di-Acidic Motifs", Mol. Biol. Cell, Jan. 2000, vol. 11(1), pp. 13-22.
Yee, J-K., et al., "A General Method for the Generation of High-Titer, Pantropic Retroviral Vectors: Highly Efficient Infection of Primary Hepatocytes", Proc. Natl. Acad. Sci., Sep. 27, 1994, vol. 91(20), pp. 9564-9568.
"Searching the Trace Archive with Discontiguous MegaBlast". [Retrieved from the internet Mar. 4, 2019:<URL: www.ncbi.nlm.nih.gov/Web/Newsltr/FallWinter02/blastlab.html>].
Basic Local Alignment Search Tool. [Retrieved from the internet Mar. 4, 2017:<URL:http://www.ncbi.nlm.nih.gov/BLAST>].
International Search Report and Written Opinion, from the International Searching Authority of the European Patent Office, for International Patent Application PCT/GB2018/052656, dated Nov. 6, 2018, pp. 1-48.

(Continued)

*Primary Examiner* — Barry A Chestnut
(74) *Attorney, Agent, or Firm* — McDonnell Boehnen Hulbert & Berghoff LLP

(57) ABSTRACT

The present invention relates to nucleic acid molecules comprising viral genes or derivatives thereof for use in the production of retroviral packaging vectors, and retroviral packaging and producer cell lines. In one embodiment, the nucleic acid molecules comprise env and gag-pol genes wherein the coding sequences of the env and gag-pol genes are in opposing orientations.

16 Claims, 9 Drawing Sheets
Specification includes a Sequence Listing.

(56) References Cited

OTHER PUBLICATIONS

Trinklein, N.D., et al., "An Abundance of Bidirectional Promoters in the Human Genome", Genome Research, 2004, vol. 14, pp. 62-66.
UK Search Report, dated Jun. 12, 2018, for GB1715052.5, pp. 1-4.
Benjamin Geiling et al., "A Modular Lentiviral and Retroviral Construction System to Rapidly Generate Vectors for Gene Expression and Gene Knockdown In Vitro and In Vivo" PLOS One, (Oct. 2013) vol. 8, No. 10, pp. 1-14.
Yao et al., "Tetracycline Repressor, tetR, rather than the tetR-Mammalian Cell Transcription Factor Fusion Derivatives, Regulates Inducible Gene Expression in Mammalian Cells", Human Gene Therapy, (Sep. 2008) vol. 9, pp. 1939-1950.
Chen et al., "Rapid Lentiviral Vector Producer Cell Line Generation Using a Single DNA Construct", Molecular Therapy: Methods & Clinical Development, (Dec. 2020) vol. 19, pp. 47-57.
Stewart et al., "Development of Inducible EIAV-based Lentiviral Vector Packaging and Producer Cell Lines", Gene Therapy, (2009) vol. 16, No. 6, pp. 805-814.

RETROVIRAL VECTORS

CROSS-REFERENCE

This application is a 371 U.S. national phase of PCT/GB2018/052656, filed Sep. 18, 2018, which claims priority from GB patent application no. 1715052.5, filed Sep. 19, 2017, both which are incorporated by reference in its entirety.

FIELD OF THE INVENTION

The present invention relates to nucleic acid molecules comprising viral genes or derivatives thereof for use in the production of retroviral packaging vectors, and retroviral packaging and producer cell lines. In one embodiment, the nucleic acid molecules comprise env and gag-pol genes wherein the coding sequences of the env and gag-pol genes are in opposing orientations.

BACKGROUND OF THE INVENTION

Retroviruses (including lentiviruses) are positive sense RNA viruses that undergo a complex life cycle involving the reverse transcription of their genome into deoxyribonucleic acid (DNA), which subsequently becomes integrated into the host cell genome following viral infection. They are capable of inserting their genomes, as DNA, into almost any loci in the genome of target cells and mediating long-term expression of virus genes, with the DNA being copied into each daughter cell when the infected cell divides. They generate their genome as an un-spliced mRNA molecule by using the cellular RNA polymerase for transcription. The virus genome is then transported into the cytoplasm using a virus protein called Rev. The genome is then packaged into virus particles in the cytosol using the virus encoded structural proteins Envelope (Env), Gag and Polymerase (Pol). The retrovirus genome is typically 7-10 kb in length; in the case of the commonly studied HIV virus, the genome is 9.7 kb in length. It exists in each virus particle at 2 copies per virion.

The retrovirus life cycle, and their structural flexibility, affords a number of biotechnological applications, such as the delivery of DNA into the genome of mammalian cells. Furthermore, retroviruses can be modified to contain non-retrovirus glycoproteins in their surface, endowing retrovirus particles with the cellular tropism of the virus from which the glycoprotein originated. This is particularly important when the natural retrovirus glycoprotein has a limited cellular tropism. An example of this is the GP160 glycoprotein of HIV-1, which has evolved to bind the CD4 receptor and only infects cells bearing this protein on their surface. In the case of HIV-1, virus particles are frequently modified to contain a glycoprotein that is different from the natural glycoprotein in a process called pseudotyping. Most commonly, this is achieved with the glycoprotein from vesicular stomatitis virus (VSV-G) to provide a much broader cell tropism.

When using retroviruses in the laboratory as tools, they are typically modified to form replication-incompetent vectors that can express either one or more transgenes or shRNA molecules, and these modified viruses provide versatile vectors for cellular transgene expression and engineering. The flexibility of the retrovirus packaging process also allows for varying genome sizes to be accommodated: genomes as small as 3 kb and as large as 18 kb can be packaged, although virus titre can be compromised at these extremes.

Several clinical trials have now been performed using retroviruses (and latterly lentiviruses) to infect stem cells ex vivo to express transgenes to be supplemented in the treatment of inherited single-gene disorders, before reintroducing them into patients. This is usually done on an autologous basis, although some stem cells can also be applied as heterologous transplants.

Retro/lentiviruses are also finding important applications in the field of adoptive cell transfer, most notably to allow expression of hybrid 'chimeric antigen receptors' (CAR) within T-cells before cell expansion and reinfusion into patients. The CARs generally have an extracellular antibody structure, and an intracellular structure based on the T-cell receptor, but modified (in 2nd and 3rd generation CARs) to improve the quality of cell stimulation following binding of the outside portion to its antigen. This 'CAR T cell' approach has shown impressive success using lentiviruses encoding CARs recognising CD19 in the clinical treatment of B cell lymphoma, and the first US product licence is expected to be granted to Novartis for their CD19-specific CAR T cell, known as CTL019, in the near future. The field of application is now being expanded to address other molecular targets and other malignancies. Hence, there is an expanding need for large scale lentivirus manufacture, something that is challenging to achieve using existing virus production systems.

Alongside clinical use, many laboratories frequently use lentivirus vectors for research and development, where the insertion of exogenous DNA into the cellular genome is required. The versatility of lentiviruses has allowed them to be used to introduce DNA into a wide range of cell types, including but not limited to, human and mouse stem cells, cancer cells, primary tissue cells (e.g. liver, neurons, and fibroblasts).

The infection of these cells is only made possible by coating, or pseudotyping, the virus with a broad tropism glycoprotein, most commonly the VSV-G surface glycoprotein. This protein enables the infection of cells from almost all organs and across many species, including but not limited to, humans, mice, rats, hamsters, monkeys, rabbits, donkeys and horses, sheep, cows and old world apes.

Although wild-type retro/lentiviruses can replicate in host cells, the retro/lentivirus vectors used for transgene and shRNA expression are typically disabled in a range of ways to remove their ability to replicate and cause disease. This means that in order to grow a batch of infectious virus particles which are capable of a single infection round, for experimental or clinical use, it is necessary to provide several virus genes (and thereby virus proteins) that have been genetically removed from the virus genome at the same time into the cells used for virus packaging. These genes are generally provided in three or four separate plasmids, and co-transfected into cells. The central component is a plasmid encoding the virus vector genome (including any transgenes and associated promoters to regulate transcription in target cells) containing packaging signals to direct the assembling virus particles to incorporate the corresponding RNA into the new virus particles. The genes for other virus proteins such as Gag-Pol, Tat and Rev are generally provided from other plasmids that are co-transfected; and yet another plasmid provides the glycoprotein to be incorporated into the envelope of newly-formed virus particles that will direct their infectious tropism. The gag-pol expression cassette encodes virus capsid and internal structural proteins and polymerase and protease activity. The rev gene acts to enhance nuclear export of retro/lentivirus genomes by binding to a specific region of the virus genome called the Rev Response Element (RRE).

The complexity of retrovirus and lentivirus packaging systems has resulted in a number of 'generations', each with increasing safety on the previous system. In the '1st generation' packaging systems, three plasmids were used: one plasmid encoding all of the HIV genes except for the envelope gene; a second plasmid to provide a surface glycoprotein (most often VSV-G); and a plasmid containing the virus genome to be packaged. This system has the disadvantage that the plasmid containing the virus genes contained large regions of DNA with homology to the virus genome plasmid, potentially allowing for recombination between plasmids. This could result in infectious virus being produced capable of causing disease. Other problems included the presence of many virus genes that were not needed for the virus production, including VPU, VIF, VPR and Nef.

In the '2nd generation' systems, five of the nine HIV-1 gene coding regions were removed from the system. This method also resulted in a three-plasmid system, with one plasmid containing the gag-pol genes and the ancillary genes for Tat and Rev proteins, a second plasmid encoding a glycoprotein (most often VSV-G) and a third plasmid that encoded the virus genome to be packaged. The virus genomes in this system typically contain wild-type 5' Long Terminal Repeats (LTRs) and hence require the tat gene for transcriptional activation and genome production. This system had the advantage that the reduction in homology between the virus genome and the packaging plasmids reduced the likelihood of the formation of potentially hazardous replication-competent retrovirus.

In the most recent '3rd generation' lentiviral vector system, four plasmids are used instead of three. By splitting the system into 4 plasmids (3 helper plasmids and 1 containing the vector genome plus transgene), the '3rd generation' system offers a number of advantages (primarily by increasing the number of recombination events required to form replication-competent virus). However, the '3rd generation' systems also have another significant advantage because they have a modified 5-LTR that includes a promoter, and hence transcription of the genome is not dependent on transcriptional activation by the Tat protein—thereby removing the need for Tat to be encoded in the system. They do not contain the Tat protein on any of the plasmids used. The rev gene was also placed on an individual plasmid. Therefore, in 3rd generation systems, the four plasmids contain 1: gag-pol, 2: a glycoprotein (most frequently VSV-G), 3: rev, and 4: a plasmid encoding a self-inactivating lentivirus genome containing the transgene or RNA of interest. With specific reference to the glycoprotein plasmid, several envelope glycoproteins are available and have been used, but the most widely used is the glycoprotein from Vesicular Stomatitis Virus, known as VSV-G.

Some of these lentivirus packaging genes, notably the VSV-G and gag-pol components, are widely reported to be toxic to mammalian cells (Burns et al., Proc. Natl. Acad. Sci. 90, 8033-8037 (1993); Yee et al., Proc. Natl. Acad. Sci., 90, 9564-9568 (1994); Hoffman et al., J. Gen. Virol, 91, 2782-2793 (2010). This has provided a substantial barrier to the development of stable packaging cells that express many of the required packaging proteins. Accordingly, batches of lentivirus have been prepared by an inefficient process requiring simultaneous expression of all the plasmids in cells by transient transfection. Such transfection methods are expensive, hard to reproduce at large scale, and often lead to contamination of the virus preparation with plasmids and cellular debris.

It is highly desirable to create 'packaging' cell lines for retroviruses and lentiviruses that encode some, or all, of the components required for production of new virus particles within the cellular genome. This could decrease the complexity of the plasmid transfection required for virus packaging and has the major benefit that every cell will be expressing the genes required for virus production. The ability to create cell lines that express virus proteins with a specific stoichiometry relative to each other would be another significant advantage. There have been several attempts to express virus proteins either stably or under conditional or inducible promoters, for example the STAR cells produced by Ikeda et al. (Nature Biotechnology, 21, 560-572 (2003)) used retroviral transduction of codon-optimised HIV Gag, Pol and Rev to achieve continuous expression in packaging cells. However, the titre of virus produced using these cells is typically below the industry standard of $1\times10^7$-$1\times10^8$/ml. The requirement that some genes must also be inducible, or require independent antibiotic selection agents significantly adds to the system's complexity, and makes scaling up for manufacture significantly more challenging. To date, there have been no cell lines produced that stably and constitutively express the most commonly used retrovirus and lentivirus glycoprotein VSV-G due to its reported toxicity.

Having the sequences encoding the Env protein and Gag/Pol proteins on a single plasmid/vector has the advantage of reducing the number of plasmids which are required to produce the virus particles, thus increasing the efficiency of the viral production system. However, this arrangement suffers from the significant disadvantage that it increases the likelihood of the formation of potentially hazardous replication-competent retroviruses. The chances of this occurring are substantially increased if a single mRNA is produced in cells that contains both the Env and Gag-Pol coding sequences in the same 5' to 3' orientation, where both proteins could be produced from the same mRNA molecule.

SUMMARY OF THE INVENTION

The inventors have now found that placing the coding sequences for the Env protein on one strand and Gag/Pol proteins on the opposing strand of the same plasmid/vector ensures that there is no possibility of read-through from a promoter which produces a single mRNA coding for Env and Gag-Pol sequences, thus reducing the risk of replication-competent viruses being formed.

It is therefore an object of the current invention to provide nucleic acid molecules and retroviral packaging vectors in particular which can be used to reduce the number of plasmids which are currently required to produce virus particles, thus increasing the overall efficiency of the viral production system.

DETAILED DESCRIPTION OF THE INVENTION

Figure 1:
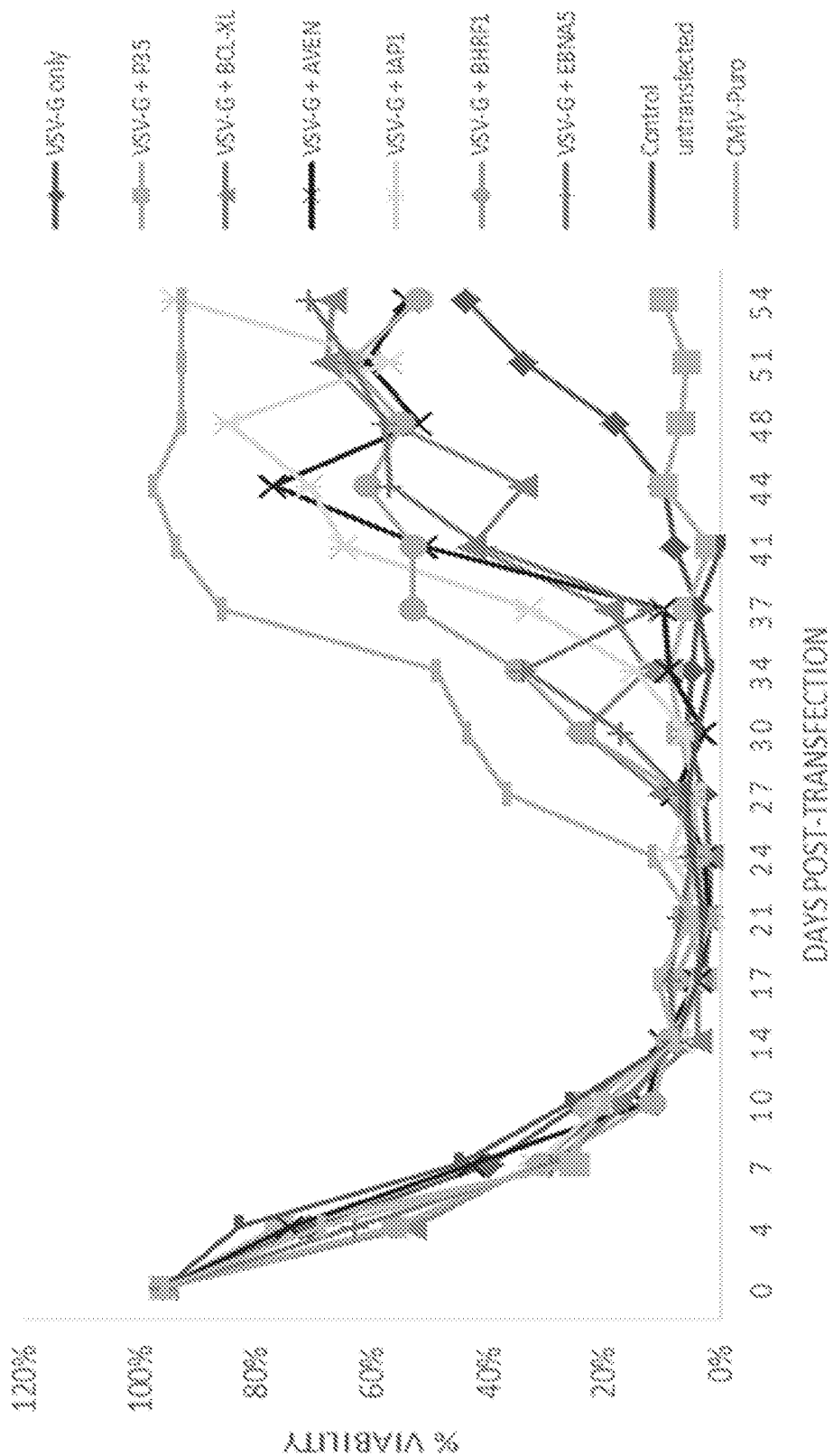
FIG. 1: Generation of stable cell lines expressing VSV-G+Apoptosis inhibitors.

In one embodiment, the invention provides a double-stranded nucleic acid molecule comprising:
(a) a first nucleic acid comprising an env gene; and
(b) a second nucleic acid comprising a gag-pol gene;
wherein the coding sequences of the first and second nucleic acids are on opposing strands of the double-stranded nucleic acid molecule, wherein the env and gag-pol genes are independently operably-associated with first and second inducible promoters having less than 95% nucleotide sequence identity between them, and wherein the double-stranded nucleic acid molecule comprises 1 or more nucleotide sequences encoding apoptosis inhibitors.

In some embodiments, the double-stranded nucleic acid molecule additionally comprises a nucleic acid comprising a rev gene. In some embodiments, the double-stranded nucleic acid molecule additionally comprises a nucleic acid comprising a transgene. Preferably, the double-stranded nucleic acid molecule is a retroviral vector, more preferably a lentiviral vector.

The nucleic acid in the double-stranded nucleic acid molecule may be DNA or RNA, preferably DNA.

Preferably, the double-stranded nucleic acid molecule is a retroviral vector. As used herein, the term "retroviral vector" refers to a vector or plasmid which is useful in the production of retroviruses. Examples of retroviral vectors include gamma-retroviral vectors (e.g. vectors derived from murine leukaemia viruses) and lentiviral vectors.

Preferably, the retroviral vector is a lentiviral vector. As used herein, the term "lentiviral vector" refers to a vector or plasmid which is useful in the production of lentiviruses. For example, the lentiviral vector may be a packaging vector, an envelope vector or a packaging/envelope vector.

The env, gag, pol and rev genes are preferably viral genes or derived from viral genes. More preferably, they are retroviral genes or derived from retroviral genes. Examples of retroviruses include lentiviruses, alpha-retroviruses, gamma-retroviruses (e.g. murine leukaemia viruses) and foamy-retroviruses. Preferably, the retrovirus is a lentivirus.

Lentiviruses are a subset of the retroviridae family that are increasingly being used for transgene delivery and protein expression, particularly in progenitor cell populations such as haematopoietic stem cells and T cells. Unlike most retroviruses, lentiviruses are able to deliver their genome, or modified forms thereof, independent of the cell cycle, and often achieve higher efficiency of cellular infection in a shorter time frame. This makes them a much more effective viral vector for both research and clinical use.

The lentivirus family consists of 10 viruses at present. These species are divided into five groups including: Bovine lentivirus group (Bovine immunodeficiency virus and Jembrana disease virus), Equine lentivirus group (Equine infectious anaemia virus, Feline lentivirus group, Feline immunodeficiency virus, Puma lentivirus), Ovine/caprine lentivirus group (Caprine arthritis encephalitis virus, Visna/maedi virus), Primate lentivirus group, (Human immunodeficiency virus 1, Human immunodeficiency virus 2, Simian immunodeficiency virus).

In a preferred embodiment, the lentivirus is Human immunodeficiency virus 1, Simian immunodeficiency virus or Equine infectious anaemia virus. In a more preferable embodiment, the lentivirus is Human immunodeficiency virus 1 or Equine infectious anaemia virus.

The env, gag, pol and rev genes may be from one or more different viruses (e.g. 2, 3 or 4 different viruses). For example, the env gene may be from Rhabdoviridae (e.g. VSV-G) whilst other the gal, pol and rev genes may be from HIV-1.

It is recognised by those in the art that the env, gag, pol and rev genes of retroviruses vary by Glade and isolate. The sequences of these genes from all such clades and isolates are encompassed herein, as well as derivatives thereof.

The first nucleic acid comprises an env gene. env is a gene that encodes the protein which forms the viral envelope. The expression of the env gene enables retroviruses to target and attach to specific cell types, and to infiltrate the target cell membrane. Examples of the env gene include the HIV-1 env gene and derivatives thereof.

In HIV, the env gene codes for the gp160 protein which forms a homotrimer, and is cleaved into gp120 and gp41 by the host cell protease, Furin. The HIV-1 env nucleotide and amino acid sequences are given in SEQ ID NOs: 1 and 2, respectively.

As used herein, the term "HIV-1 env gene" refers preferably to a nucleotide sequence having the sequence given in SEQ ID NO: 1 or a nucleotide sequence encoding SEQ ID NO: 2, or a nucleotide sequence having at least 80%, 85% 90%, 95% or 99% sequence identity thereto and which encodes a gp160 protein which is capable of forming a homotrimer and is capable of being cleaved into gp120 and gp41 polypeptide by the HIV-1 protease.

The viral envelope may be pseudotyped by using an env gene from a virus such as Vesicular Stomatitis virus (VSV), e.g. the VGV-G gene, or a derivative thereof.

The VSV-G protein is a single-pass membrane glycoprotein. It mediates a broad infectious tropism. The gene is encoded by a 1536 bp open reading frame and produces a protein consisting of 511 amino acids. The protein contains a 16 amino signal peptide at the N-terminus (amino acid sequence: MLSYLIFALAVSPILG, SEQ ID NO: 14) which is cleaved from the mature protein during export through the secretory pathway to the cell surface. The glycoprotein contains an extracellular region of 458 amino acids and a membrane spanning region (transmembrane region) of 21 amino acids followed by an intracellular (cytosolic) C-terminal region of 22 amino acids. The shuttling of VSV-G protein from the endoplasmic reticulum is rapid, and this is achieved by the specific trafficking signals in the C-terminal tail, including a DxE motif (where x is any amino acid) within the broader trafficking signal Tyr-Thr-Asp-Ile-Glu-Met that contains the DxE motif (Sevier et al., Mol. Biol.

Cell. 2000 January; 11(1): 13-22). The efficiency of export of VSV-G protein may in part contribute to its effectiveness for retrovirus and lentivirus production. The VSV-G receptor is frequently described as a non-specific fusogenic protein; however, is was recently determined the VSV-G binds to the low-density lipid receptor (LDL-R) (Finkelstein et al., Proc. Natl. Acad. Sci. USA 2013; 110(18):7306-7311), which explains its broad cellular tropism and broad application in retrovirus and lentivirus pseudotyping.

As used herein, the term "VGV-G gene" refers preferably to a nucleotide sequence having the sequence given in SEQ ID NO: 3 or a nucleotide sequence encoding SEQ ID NO: 4, or a nucleotide sequence having at least 80%, 85% 90%, 95% or 99% sequence identity thereto and which encodes a polypeptide which is capable of attaching to the LDL receptor.

The second nucleic acid comprises a gag-pol gene. As used herein, the term "gag-pot" includes contiguous/overlapping gag-pol genes and independent gag and pol genes.

The Gag-Pol protein of lentiviruses is produced as a single poly-protein that encodes a protease that enables the proteolytic cleavage of the Gag-Pol protein into a number of smaller proteins serving a number of virus functions. The HIV-1 Gag protein is produced from the first translated open reading frame from the 5'-end of the virus genome and contains a sequence known as the frame-shift sequence. This signal causes the translating ribosome to shift back on the mRNA molecule one base during translation approximately every 1 in 20 translation runs. This process produces the Gag-Pol protein. The result is that lentivirus produce Gag and Gag-Pol at an approximate ratio of 1:20. The Gag protein encodes three major structural proteins: p18, p24 and p15. The Pol protein segment also encodes three major proteins called p10 (protease), p66/55 (reverse transcriptase) and p32 (integrase). The protease is responsible for all of the cleavage events required to produce each of these proteins by proteolytic cleavage. However, the protease recognition sequences that define these cleavage events are poorly defined, suggesting that the protease has broad specificity. This is therefore likely to result in the cleavage of proteins that are not virus related. Indeed, the expression of Gag-Pol proteins is reported to be highly toxic to cells because of this (Blanco et al., The Journal of Biochemistry, 278, 2, 1086-1093, 2003).

In some viruses, the coding sequences of the gag and pol genes overlap. The coding sequences of the gag and pol genes of the invention may be contiguous, non-contiguous, overlapping or non-overlapping.

Preferably, the gag-pol sequence is from a lentivirus. Examples of the gag, pol and gag-pol genes include HIV-1 gag-pol genes and derivatives thereof.

In HIV-1, the reading frames of the gag and pol genes overlap, i.e. in a gag-pol gene. The HIV-1 gag-pol nucleotide sequence is given in SEQ ID NO: 5.

As used herein, the term "HIV-1 gag-pol gene" refers preferably to a nucleotide sequence having the sequence given in SEQ ID NO: 5, or a nucleotide sequence having at least 80%, 85% 90%, 95% or % sequence identity thereto and which encodes matrix, capsid and nucleocapsid proteins, and a reverse transcriptase, integrase, and protease.

In the double-stranded nucleic acid molecules of the invention, the polypeptide-coding sequences of the first and second nucleic acids are on opposing strands of the double-stranded nucleic acid molecule. The two strands of double-stranded nucleic acid molecules are often referred to as the sense/anti-sense strands or positive/negative strands. Therefore, if one defines the nucleic acid strand which includes the coding sequence of the env gene as the sense or positive strand, the coding sequences for the gag and pol genes will be on the antisense or negative strand.

In some embodiments, the double-stranded nucleic acid molecule additionally comprises a nucleic acid comprising a rev gene. Rev is a trans-activating protein that is essential to the regulation of HIV-1 protein expression. A nuclear localization signal is encoded in the rev gene, which allows the Rev protein to be localized to the nucleus, where it is involved in the export of unspliced and incompletely spliced mRNAs. Rev binds to a region in the lentivirus genome called the Rev Response Element which allows the nuclear export of unspliced, full length genomes, which is essential for lentivirus production. Examples of the rev gene include the HIV-1 rev gene and derivatives thereof. The HIV-1 rev nucleotide and Rev amino acid sequences are given in SEQ ID NOs: 6 and 7, respectively.

As used herein, the term "HIV-1 rev gene" refers preferably to a nucleotide sequence having the sequence given in SEQ ID NO: 6 or a nucleotide sequence encoding SEQ ID NO: 7, or a nucleotide sequence having at least 80%, 85% 90%, 95% or 99% sequence identity thereto and which encodes a protein which is capable of binding to the Rev Response Element (RRE).

In some other embodiments, the double-stranded nucleic acid molecule does not comprise a nucleic acid comprising a rev gene.

VSV-G is generally cytotoxic to cells. It is capable of inducing cell fusion and the formation of syncytia. Some of the gag-pol gene products are also cytotoxic. In particular, the pol gene encodes a protease that cleaves proteins within the cell and leads to cell death.

The expression of one or more apoptosis inhibitors mitigates or prevents apoptosis of the cell which would otherwise have been initiated by the cytotoxicity of the cytotoxic polypeptide(s). Therefore, the double-stranded nucleic acid of the invention additionally comprises one or more nucleotide sequences encoding apoptosis inhibitors. The one or more apoptosis inhibitors may independently, for example, be polypeptide or RNA.

Preferably, the double-stranded nucleic acid of the invention additionally comprises 1, 2, 3, 4 or 5, more preferably, 1 or 2 nucleotide sequences encoding apoptosis inhibitors. In some embodiments, the apoptosis inhibitor is an inhibitor of the APAF-1 (e.g. AVEN), Caspase 9 (e.g. IAP or XIAP), BAK, BAX, BOK or BAD (e.g. BCL2, E1B-19K or BCL-XL) pathway. Preferably, more than one gene is used that inhibits more than one apoptosis pathway or step (e.g. AVEN combined with E1B-19K) to provide improved resistance to apoptosis.

In some embodiments, the one or more of the apoptosis inhibitor is one which inhibits an apoptotic protein whose production is stimulated by loss of cell membrane integrity, by cell-cell fusion or by syncytia formation or one which is stimulated by a protease that cleaves proteins within the cell.

Examples of apoptosis-inhibiting polypeptides include Celovirus GAM1, Adenovirus E4 Orf6, Adenovirus E1B 55K, Adenovirus E1B 19K, Myxomavirus M11L, Cytomegalovirus IE1, Cytomegalovirus 1E2, Baculovirus p35, Baculovirus IAP-1, Herpesvirus US3, Herpesvirus Saimiri ORF16, Herpes Simplex 2 LAT ORF 1, Human XIAP, African Swine Fever ASFV-5-HL (LMW-5-HL/A179L), Kaposi's Sarcoma virus KSbcl2, Vaccinia virus SPI-2, Cowpoxvirus CrmA, Epstein Barr virus BHRF1, Epstein Barr virus EBNA-5, Epstein Barr virus BZLF-1, Papillomavirus E6, Human Aven, Human BCL2 and Human BCL-XL.

In some embodiments, one or more of the apoptosis inhibitors is an RNA, preferably an antisense or shRNA. Other examples of RNA apoptosis inhibitors include Herpesvirus LAT and Adenovirus VA1.

Preferably, the apoptosis inhibitors are selected from the group consisting of IAP1, EBNA5 and BCL-XL. Particularly-preferred combinations of apoptosis inhibitors include: IAP1+EBNA5; IAP1+BCL-XL; and EBNA5+BCL-XL. Nucleotide sequences of apoptosis inhibitors IAP1, EBNA5 and BCL-XL are given herein as SEQ ID NOs: 11, 12 and 13, respectively.

Particularly preferred are double-stranded nucleic acids of the invention which additionally comprises a nucleotide sequence encoding an apoptosis inhibitor comprising SEQ ID NO: 11, 12 or 13, or a nucleotide sequence having at least 80%, 85%, 90%, 95% or 99% sequence identity thereto.

The production of stable cell lines in mammalian culture typically requires a method of selection to promote the growth of cells containing any exogenously-added DNA. Preferably, the double-stranded nucleic acid molecules of the invention additionally comprise a selection gene or an antibiotic resistance gene. To this end, a range of genes are known that provide resistance to specific compounds when the DNA encoding them is inserted into a mammalian cell genome.

Preferably, the selection gene is puromycin N-acetyltransferase (Puro), hygromycin phosphotransferase (Hygro), blasticidin s deaminase (Blast), Neomycin phosphotransferase (Neo), glutathione S-transferase (GS), zeocin resistance gene (Sh ble), or dihydrofolate reductase (DHFR). Each of these genes provides resistance to a small molecule known to be toxic to mammalian cells, or in the case of GS provides a method for cells to generate glutathione in the absence of glutathione in the growth media.

In a preferred embodiment of the invention, the resistance gene is Puro. This gene is particularly effective because many of the cell lines used in common tissue culture are not resistant; this cannot be said for Neo where many, particularly HEK 293 derivatives, are already Neo resistant due to previous genetic manipulations by researchers (e.g. HEK 293T cells). Puro selection also has the advantage of being toxic over a short time window (<72 hours), and hence it allows variables to be tested rapidly and cells that do not harbour the exogenous DNA to be inserted into the genome are rapidly removed from the culture systems. This cannot be said of some other selection methods such as Hygro, where toxicity is much slower onset.

The development of stable cell lines using selection genes (e.g. Puro) requires that the resistance gene must be expressed in the cells. This can be achieved through a variety of methods including, but not limited to, internal ribosome entry sites (IRES), 2A cleavage systems, alternative splicing, and dedicated promoters.

In a preferred embodiment of the invention, the selection gene will be expressed from a dedicated promoter. This promoter will preferably transcribe in human cells at lower levels than the dedicated promoters driving the VSV-G or gag-pol genes.

Each of the genes in the double-stranded nucleic acid molecule which encode a polypeptide or RNA is preferably operably-associated with one or more regulatory elements. This ensures that the polypeptide or RNA is expressed at the desired level and at the desired time.

In this context, the term "regulatory elements" includes one or more of an enhancer, promoter, intron, polyA, insulator or terminator.

The genes used in the vectors herein are preferably separated by polyA signals and/or insulators in an effort to keep transcriptional read-through to other genes to a minimum and also to insulate the genes which it is desired to repress (VSV-G and gag-pol) under normal circumstances from genes which it is desired to be expressed (e.g. TetR and the apoptosis inhibitors).

While some advantages may be obtained by using copies of the same regulatory element (e.g. promoter sequence) with more than one polypeptide or RNA-encoding nucleotide sequence (in terms of their co-ordinated expression), in this context of this invention, it is highly desirable to use different regulatory elements with each polypeptide or RNA-encoding nucleotide sequence.

Preferably, therefore, the env and gag-pol genes are operably associated with different regulatory elements, e.g. different promoter, different intron, different polyA, different insulator and/or different terminator sequences.

More preferably, the degree of nucleotide sequence identity between the env promoter and the gag-pol promoter is less than 95% or less than 90%, more preferably less than 85%, 80%, 70% or 60%. More preferably, the degree of nucleotide sequence identity between the env terminator and the gag-pol terminator is less than 95% or less than 90%, more preferably less than 85%, 80%, 70% or 60%. In this way, the risk of homologous recombination between these regulatory elements is reduced.

The env and gag-pol genes are independently operably associated with inducible promoter sequences. The apoptosis inhibitor genes, when present, will also be operably associated with one or more promoters; these may be inducible, repressible or constitutive.

The inducible promoters may ones which are inducible with doxycycline, tetracycline, IPTG or lactose. Preferably, the inducible promoter element comprises a plurality of Tet operator sequences to which the Tet repressor protein (TetR) is capable of binding. In the bound state, tight suppression of transcription is obtained. However, in the presence of doxycycline (or less preferably tetracycline), suppression is alleviated, thus allowing the promoter to gain full transcriptional activity. Such an inducible promoter element is preferably placed downstream of another promoter, e.g. the CMV promoter.

The TetR binding site may have a wild-type sequence, many of which are known in the art. Preferably, the TetR binding site has been subject to one or more improvements by incorporating minor sequence changes. A preferred version that may be used in an embodiment of the invention has the sequence: tccctatcagtgatagaga (SEQ ID NO: 8). Alternative versions of the repressor element that bind the TetR protein or derivatives of the TetR protein may also be used in an embodiment of the invention provided that the TetR repressor protein binds to the TetR binding sequence variant used. Some repressor/binding site variants will have higher than wild-type affinity for each other; these are preferable in an embodiment of the invention.

The TetR gene will be integrated into the chromosome of a human (host) cell. The gene may or may not be integrated adjacent to, or in conjunction with, the env or gag-pol genes.

In a preferred embodiment, the coding strand of the TetR gene, when placed adjacent to an env or gag-pol gene, is in the opposing strand of DNA in the reverse orientation 5' to 3' to the coding sequence of the Gag-Pol proteins. In some embodiments, the TetR gene is co-expressed with the gag-pol gene.

In one embodiment of the invention, the nucleotide sequence of the TetR protein is as given in SEQ ID NO: 9 or a nucleotide sequence having at least 80%, more preferably at least 85%, 90% or 95% sequence identity thereto and which codes for a TetR protein.

In another embodiment of the invention, the amino acid sequence of the TetR protein is as given in SEQ ID NO: 10 or an amino acid sequence having at least 80%, more preferably at least 85%, 90% or 95% sequence identity thereto and which encodes a TetR protein.

In some preferred embodiments, the promoters which are operably associated with the env gene (preferably the VSV-G gene) and the gag-pol genes are inducible promoters which are commonly inducible (i.e. inducible together).

More preferably, the promoters which are operably associated with the env gene (preferably the VSV-G gene) and the gag-pol genes both comprise TetR binding sites which allow simultaneous repression and co-expression of the env gene (preferably the VSV-G gene) and the gag-pol genes.

Preferably, the apoptosis inhibitor promoters are selected from the group consisting of RSV, CMV, SV40, PGK and ubiquitin promoters.

In embodiments of the invention wherein more than one apoptosis inhibitor is used, each apoptosis inhibitor is preferably driven independently by a different promoter; and each promoter is preferably of a different type (e.g. CMV, SV40, etc.).

It is preferable that each nucleic acid encoding an apoptosis inhibitor is expressed under the control of a promoter that provides the cell with optimal apoptosis inhibition.

In some preferred embodiments, the double-stranded nucleic acid molecule of the invention comprises the use of the following promoter-apoptosis inhibitor combinations:
RSV—Human Inhibitor of Apoptosis (IAP) 1
RSV—Epstein Barr EBNA5
RSV—BCL-XL
SV40—Human Inhibitor of Apoptosis (IAP) 1
SV40—Epstein Barr EBNA5
SV40—BCL-XL
PGK—Human Inhibitor of Apoptosis (IAP) 1
PGK—Epstein Barr EBNA5
PGK—BCL-XL
Ubiquitin—Human Inhibitor of Apoptosis (IAP) 1
Ubiquitin—Epstein Barr EBNA5
Ubiquitin—BCL-XL Preferably, the double-stranded nucleic acid molecule comprises a combination of at least two of IAP1, EBNA5 and BCL-XL, wherein the expression of IAP1, EBNA5 and BCL-XL is preferably driven by any of the promoters selected from RSV, CMV, SV40, PGK, GRP78, EF1-Alpha, SFFV, CHEF-1, Adenovirus E1A, Chicken Beta Actin, CAG, CMV-Beta-Globin, and ubiquitin promoters.

The double-stranded nucleic acid molecule of the invention may additionally comprise at least one transgene. In other embodiments, there is provided a kit comprising a double-stranded nucleic acid molecule of the invention and a vector or plasmid comprising a transgene.

In some embodiments, the env and gag-pol genes are flanked by site-specific recombination sites, preferably LoxP or FRT sites, more preferably LoxP sites.

The invention particularly provides a retroviral packaging plasmid comprising a double-stranded nucleic acid of the invention.

Examples of preferred embodiments of the invention include double-stranded nucleic acid molecules comprising the following elements in this order:
TetR gene (reverse orientation)—(inducible, e.g. Tet repressible promoter) VSV-G gene—(constitutive, e.g. EF1a, promoter) Puromycin resistance—gag-pol gene (reverse orientation; inducible, e.g. Tet repressible, promoter)—Apoptosis inhibitor 1—Apoptosis inhibitor 2.
TetR gene (reverse orientation)—(inducible, e.g. Tet repressible promoter) VSV-G gene—(IRES, promoter) Puromycin resistance—gag-pol gene (reverse orientation; inducible, e.g. Tet repressible, promoter)—Apoptosis inhibitor 1—Apoptosis inhibitor 2.
(constitutive promoter) VSV-G gene—(constitutive promoter) Puromycin resistance—gag-pol gene (reverse orientation; constitutive promoter)—Apoptosis inhibitor 1—Apoptosis inhibitor 2.
(constitutive promoter) VSV-G gene—IRES—Puromycin resistance—gag-pol gene (reverse orientation; constitutive promoter)—Apoptosis inhibitor 1—Apoptosis inhibitor 2.

There are many established algorithms available to align two amino acid or nucleic acid sequences. Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid or nucleic acid sequences for comparison may be conducted, for example, by computer-implemented algorithms (e.g. GAP, BESTFIT, FASTA or TFASTA), or BLAST and BLAST 2.0 algorithms.

Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402. Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used.

With regard to nucleotide sequence comparisons, MEGA-BLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention.

The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page (www.ncbi.nlm.nih.gov/Web/Newsltr/FallWinter02/blast-lab.html). This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are:

word size: 11 or 12; template: 16, 18, or 21; template type: coding (0), non-coding (1), or both (2).

In some embodiments, the BLASTP 2.5.0+algorithm may be used (such as that available from the NCBI using the default parameters.

In other embodiments, a BLAST Global Alignment program may be used (such as that available from the NCBI) using a Needleman-Wunsch alignment of two protein sequences with the gap costs: Existence 11 and Extension 1.

The invention also provides a kit comprising:
 (i) a retroviral packaging vector comprising a double-stranded nucleic acid of the invention, together with one or more of the following:
 (ii) a retroviral Transfer Vector comprising a transgene and a retroviral rev gene;
 (iii) cells of a cell line suitable for the production of virus particles.

The invention also provides a kit comprising:
 (i) a retroviral packaging vector comprising a double-stranded nucleic acid of the invention which additionally comprises a rev gene,
together with one or more of the following:
 (ii) a retroviral Transfer Vector comprising a transgene;
 (iii) cells of a cell line suitable for the production of virus particles.

The retroviral Transfer Vector contains sites (e.g. LTRs) for insertion of a transgene into a cell genome. Preferably, the 5'-LTR includes a promoter in the Transfer Vector, thus obviating the need for the Tat protein.

The kit may also contain materials for purification of the viral particles such as those involved in the density banding and purification of viral particles, e.g. one or more of centrifuge tubes, Iodixanol, dialysis buffers and dialysis cassettes.

The invention also provides a mammalian cell comprising a double-stranded nucleic acid of the invention. The double-stranded nucleic acid of the invention may be stably integrated into the nuclear genome of the mammalian cell or present within a vector or plasmid within the cell. Preferably, the double-stranded nucleic acid of the invention is stably integrated into the nuclear genome of the mammalian cell.

The cells may be isolated cells, e.g. they are not situated in a living animal. Examples of mammalian cells include those from any organ or tissue from humans, mice, rats, hamsters, monkeys, rabbits, donkeys, horses, sheep, cows and apes. Preferably, the cells are human cells. The cells may be primary or immortalised cells. Preferred cells include HEK-293, HEK 293T, HEK-293E, HEK-293 FT, HEK-293S, HEK-293SG, HEK-293 FTM, HEK-293SGGD, HEK-293A, MDCK, C127, A549, HeLa, CHO, mouse myeloma, PerC6, 911, and Vero cell lines. HEK-293 cells have been modified to contain the E1A and E1B proteins and this allows the creation of viruses that have a deletion of the E1A and E1B regions to be grown in this cell line by trans-complementation. Similarly, PerC6 and 911 cells contain a similar modification and can also be used. Most preferably, the human cells are HEK293, HEK293T, HEK293A, PerC6 or 911. Other preferred cells include CHO and VERO cells. Preferably, the cells of the invention are capable of inducibly expressing the env and gag-pol genes.

The invention also provides a retroviral packaging cell, preferably a mammalian cell, more preferably a human cell), comprising a double-stranded nucleic acid molecule of the invention.

In a further embodiment, therefore, there is provided a process for producing a retroviral packaging cell, the process comprising the steps:
 (i) stably integrating a double-stranded nucleic acid molecule of the invention into a mammalian cell,
thereby producing a mammalian cell that expresses retroviral env and gag-pol genes, and optionally the rev gene.

The invention also provides the use of a retroviral packaging cell of the invention in the production of a retrovirus particle.

The invention also provides a process for producing retroviruses, the process comprising the steps:
 (a) introducing a retroviral Transfer Vector comprising 5' and 3' retrovirus LTRs and a retrovirus packaging signal and a retroviral rev gene into a retroviral packaging cell of the invention, wherein the retroviral packaging cell comprises retroviral env and gag-pol genes stably integrated into its genome;
 (b) culturing the cell under conditions such that retroviruses are assembled and secreted by the cell; and
 (c) harvesting packaged retrovirus from the supernatant.

The invention also provides a process for producing retroviruses, the process comprising the steps:
 (a) introducing a retroviral Transfer Vector comprising a transgene into a retroviral packaging cell of the invention, wherein the retroviral packaging cell comprises retroviral env, gag-pol and rev genes stably integrated into its genome;
 (b) culturing the cell under conditions such that retroviruses are assembled and secreted by the cell; and
 (c) harvesting packaged retrovirus from the supernatant.

Preferably, the viral vectors are replication-defective or replication-incompetent.

As used herein, the term "introducing" one or more vectors into the cell includes transformation, and any form of electroporation, conjugation, infection, transduction or transfection, inter alia. Processes for such introduction are well known in the art (e.g. Proc. Natl. Acad. Sci. USA. 1995 Aug. 1; 92 (16):7297-301). Preferably, the harvested retroviruses are subsequently purified.

The disclosure of each reference set forth herein is specifically incorporated herein by reference in its entirety.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Identification of Factors Supporting Viral Protein Expression

The viral glycoprotein, VSV-G, from Vesicular Stomatitis Virus, was co-expressed with a panel of apoptosis inhibitors. We were able to identify several molecules which supported the constitutive expression of VSV-G, and were able to establish a stable cell line via antibiotic selection. This data was subsequently used to select the preferred apoptosis inhibitors to be included in the final Lentiviral packaging and producer cell lines, described in the latter Examples.

HEK293 suspension cells were transfected using PEI reagent with a range of expression vectors encoding VSV-G operatively linked to a Puromycin selection marker via IRES, as well as a number of apoptosis inhibitor genes. Stable pools were established by media exchange in selective media every 3-4 days. Due to the toxicity of the VSV-G gene, which is constitutively expressed, stable pools took an extended period to establish. The results are shown in FIG. 1. Selected apoptosis inhibitors, as illustrated, increased the rate of stable pool recovery, relative to the VSV-G only construct.

Figure 2:
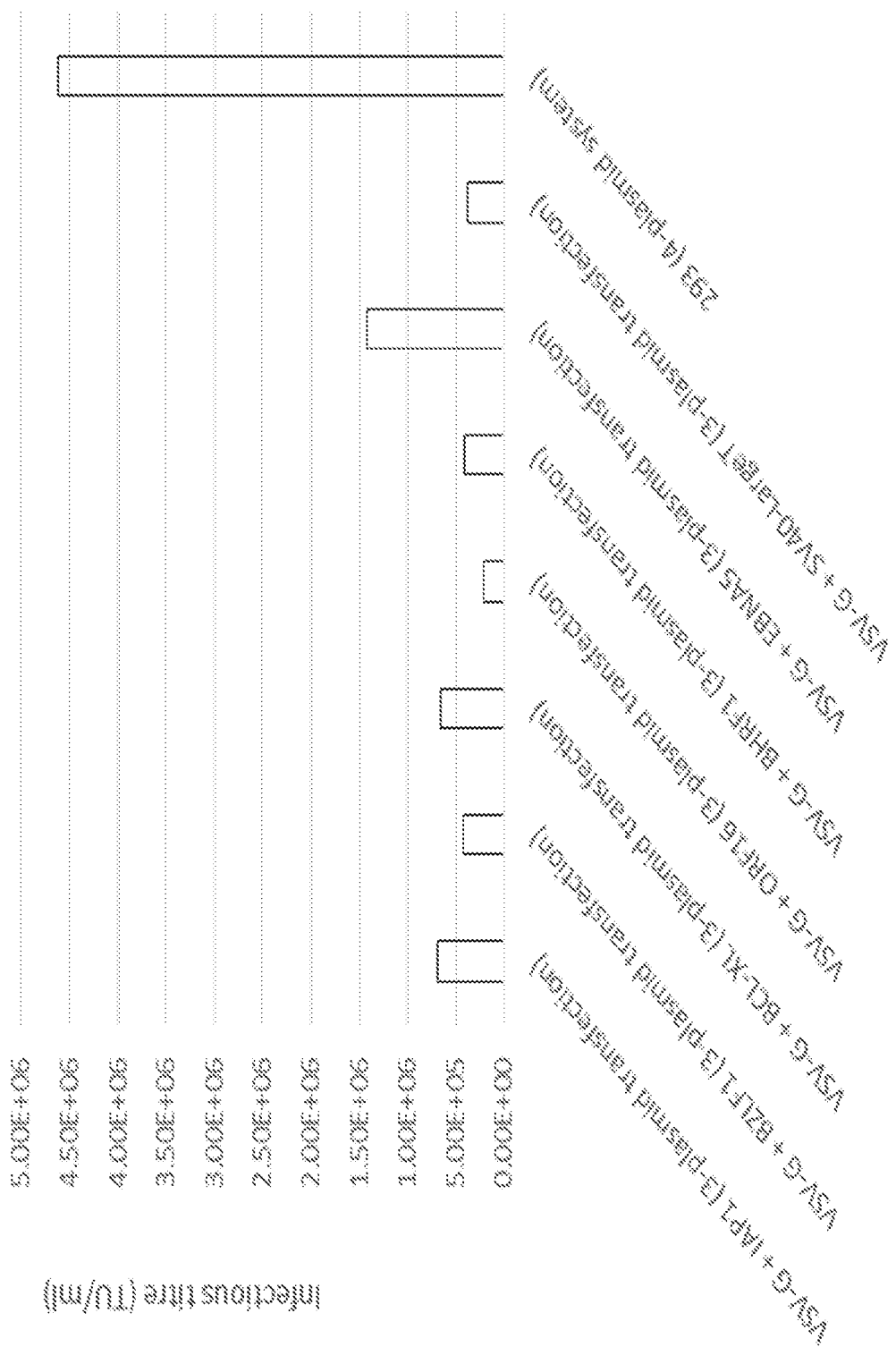
FIG. 2: Expression of Lentiviral particles from VSV-G stable cell lines.

Stable pools were transfected using PEI reagent with 3 vectors encoding all of the factors required for Lentiviral expression (GagPol, Rev, Genome), with the exception of VSV-G which was expressed from the stably-integrated copies. For control purposes, the parental HEK293 line was transfected with the same plasmid set, but also including the VSV-G vector. The genome contained the eGFP gene and this was used for titration (to estimate viral infectious titre) in adherent HEK293 cells. The results are shown in FIG. 2. This experiment demonstrated that the constitutive cell lines, when supported by the co-expression of apoptosis inhibitors, were able provide functional VSV-G expression. Such expression is believed to be sufficient in the context of stable producer of packaging cell line to support high-level viral particle production.

Figures 3, 4:
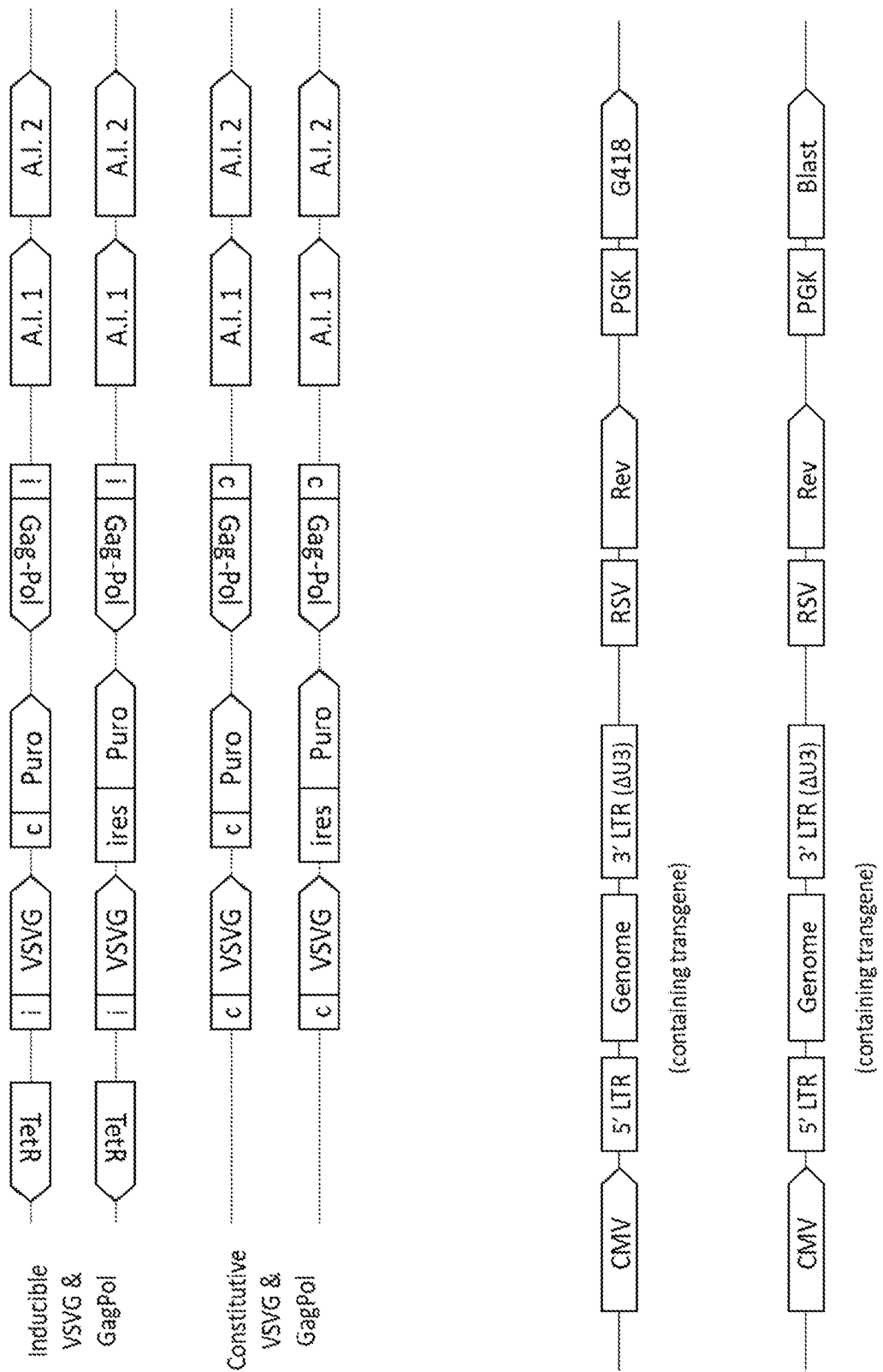
FIG. 3: Schematic illustration of the arrangement of the main expression cassettes in the vectors expressing VSV-G and gag-pol genes. An inducible promoter is denoted: i and a constitutive one: c. A.I. indicate apoptosis inhibitors.
FIG. 4: Schematic diagram illustrating the arrangement of the main expression cassettes. LTR denotes long terminal repeat, RSV denotes Rous sarcoma virus promoter, PGK denotes the human Phosphoglycerate kinase promoter, G418 denotes the G418 (geneticin) resistance gene and Blast denotes the blasticidin resistance gene.

Example 2: Production of Constructs for Lentiviral Packaging and Producer Cell Line Construction Four constructs were produced as illustrated in FIG. 3. The constructs paired VSV-G and gag-pol genes together using a Puromycin selection marker, and rev and genome together using either a G418 or Blasticidin selection marker.

Each cassette can be broken down into functional components as follows:
VSV-G Cassette
  Inducible promoter (PGK CMV fusion promoter converted into an inducible promoter by the addition of two TetO sites in strategic positions) or Constitutive promoter (a PGK CMV fusion promoter)
  5'UTR=human triose phosphate isomerase (TPI) intron
  CDS (VSV-G codon optimised for expression in HEK293 cells)
  Rabbit beta-globin polyA signal
GagPol Cassette
  Inducible promoter (CMV converted into an inducible promoter by the addition of two TetO sites in strategic positions) or Constitutive promoter (CMV)
  5'UTR (Human beta-globin intron)
  CDS (wild type HIV1 GagPol)
  RRE from HIV-1
  Human beta-globin polyA signal
TetR Protein Expression Cassette (Only Present in the Inducible Vectors)
  Promoter (CMV)
  TetR sequence (codon optimised for expression in HEK293 cells)
  PolyA
Antibiotic Resistance Marker
  Puro (either IRES-Puro or EF1-alpha-puro)
Apoptosis Inhibitor Cassettes
  IAP1 and EBNA5
Rev/Genome Vector The Rev/genome vector was designed to be stably integrated into the VSV-G/GagPol stable cell line, in order to generate a producer cell line containing all factors required for Lentiviral particle production. A schematic showing the Rev/Genome constructs is shown in FIG. 4.

Each of the Rev/Genome vector cassettes can be broken down into functional components as follows:
Genome
  Third generation lentiviral genome
  Chimeric 5' LTR fused to a heterologous CMV promoter driving transcription of the lentiviral genome.
Transgene Cassette
  The transgene is green fluorescent protein (GFP) or an anti-CD19 chimeric antigen receptor (CAR).
  The transgene is expressed from the Spleen focus forming virus (SFFV) promoter.
Rev Cassette
  Constitutive RSV promoter
  Rev CDS
Antibiotic Resistance Marker
  PGK-G418 or PGK-Blast

Example 3: Analysis of Constructs for Lentiviral Packaging and Producer Cell Line Construction in Transient Context In order to evaluate the functionality of the vectors to be used in stable cell lines, they were first used to generate Lentiviral particles in transient experiments in adherent cells. This allowed benchmarking against standard 4-vector transient expression vectors.

Adherent 293T cells were transfected with 2, 3 or 4-plasmid lentiviral packaging systems which included constructs (constitutive or inducible) generated for the purposes of stable lentivirus producer cell line construction. Throughout, eGFP was used as the transgene in the genome vector.

The lentivirus containing supernatant was collected after 72 hours, serially diluted in DMEM and used to infect adherent 293 cells. After 72 hours, the cells were trypsinized and analysed on the flow cytometer for eGFP signal.

Data from serial dilution at which 10-20% eGFP positive (i.e. transduced) cells had been achieved was then used to calculate infectious particle concentration. This was used to gauge the performance of the different packaging/producer constructs under evaluation.

Day 0: 293T cells were seeded into 6-well plates in DMEM supplemented with 10% Foetal Bovine serum at a pre-defined density, ready for transfection the following day. Cells were incubated overnight at 37° C., 5% $CO_2$ in a humidified incubator.

Day 1: Cells were transfected using branched PEI with the combinations of plasmids as detailed in Table 1 with or without Doxycycline, regardless of whether the constructs under evaluation were constitutive or inducible.

Day 3: 293 cells were seeded into 48-well plates in DMEM+10% FBS at a pre-defined density, ready for infection the following day. Cells were incubated overnight at 37° C., 5% $CO_2$ in a humidified incubator.

Day 4: Harvest of lentiviral supernatants followed by centrifugation to remove cellular debris. Lentiviruses were serially diluted and used to infect 293 cells.

Day 7: Harvest of transduced cells and analysis by flow cytometry. The dilution at which 10-20% eGFP positive (i.e. transduced) cells had been achieved was then used to calculate infectious particle concentration.

Combinations of 4, 3 and 2 plasmid system constructs were tested for the production of transient lentivirus in adherent 293T cells. The combinations are shown below in Table 1.

TABLE 1

4 plasmid system (4P) - Constant components GagPol, Rev and eGFP genome on individual plasmids
Varied component VSV-G

| VSVG | Apoptosis inhibitor | Constitutive/ Inducible | Promoter |
|---|---|---|---|
| P6189 | None | Constitutive | |
| P7847 | None | Constitutive | IRES Puro |
| P8170 | IAP1 | Constitutive | promoter(EF1a)-Puro |
| P8176 | BCL-XI | Constitutive | promoter(EF1a)-Puro |
| P8238 | EBNA5 | Constitutive | IRES Puro |
| Q2589 | IAP1 | Inducible | |
| Q2583 | BCL-XI | Inducible | promoter(EF1a)-Puro |
| Q2586 | EBNA5 | Inducible | promoter(EF1a)-Puro |

3 plasmid system (3P) - Constant components: Rev and eGFP genome on individual plasmids
Varied component VSV-G/GagPol on a single plasmid

| VSV-G/GagPol | Apoptosis inhibitor | Constitutive/ Inducible | Promoter |
|---|---|---|---|
| P6998 | none | Constitutive | |
| Q1619 | none | Constitutive | IRES Puro |
| Q1781 | none | Constitutive | promoter(EF1a)-Puro |
| Q1852 | IAP1 EBNA5 | Constitutive | promoter(EF1a)-Puro |
| Q1784 | IAP1 EBNA5 | Constitutive | IRES Puro |
| Q1621 | none | Inducible | promoter(EF1a)-Puro |
| Q1850 | IAP1 EBNA5 | Inducible | promoter(EF1a)-Puro |

3 plasmid system (3P) - VSV-G and GagPol on individual plasmids, combination Rev and eGFP genome Q1847
2 plasmid system (2P) - Constant components: Rev and eGFP genome on a single plasmid
Varied component VSV-G/GagPol on a single plasmid

| VSV-G/GagPol | Apoptosis inhibitor | Constitutive/ Inducible | Promoter |
|---|---|---|---|
| P6998 | none | Constitutive | |
| Q1619 | none | Constitutive | IRES Puro |
| Q1781 | none | Constitutive | promoter(EF1a)-Puro |
| Q1852 | IAP1 EBNA5 | Constitutive | promoter(EF1a)-Puro |
| Q1784 | IAP1 EBNA5 | Constitutive | IRES Puro |
| Q1621 | none | Inducible | promoter(EF1a)-Puro |
| Q1850 | IAP1 EBNA5 | Inducible | promoter(EF1a)-Puro |

A number of conclusions were drawn from this data:

All components within the Lentiviral vectors are fully functional.

Two plasmid systems are capable of giving high Lentiviral titres, and in many cases outperform, or are equivalent to, 3 or 4-plasmid systems.

Figure 5:
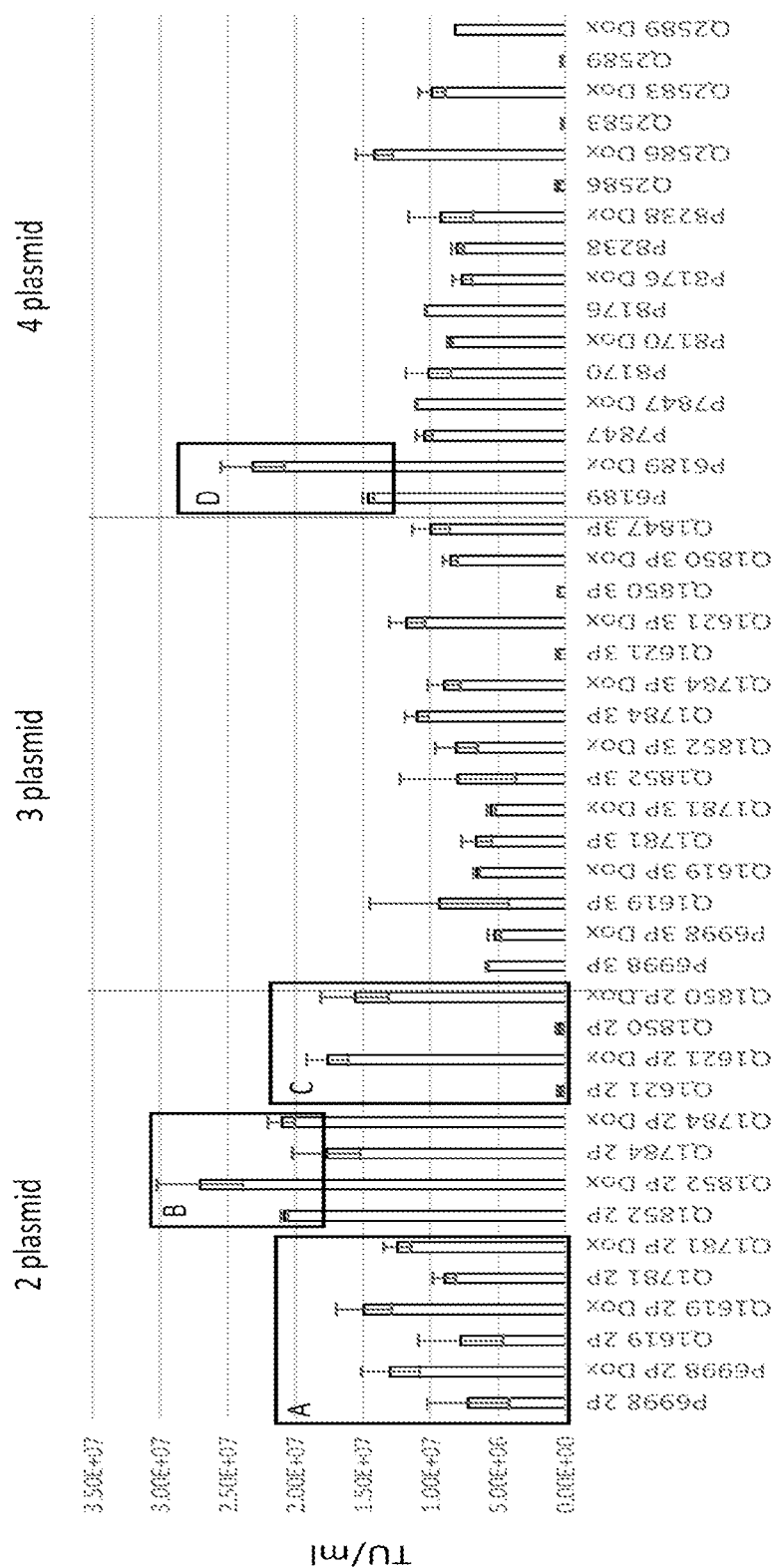
FIG. 5: Transient evaluation of Lentiviral vectors for packaging and producer cell line generation.

Constitutive VSV-G/GagPol constructs also encoding apoptosis inhibitors in the 2-plasmid system showed boosted lentivirus production when compared to the identical constructs lacking these cassettes (FIG. 5, Box A versus Box B).

Inducible VSV-G/GagPol constructs with or without apoptosis inhibitors, showed high-level viral particle expression, only slightly below constitutive constructs (FIG. 5, Box C versus Box B).

Inducible constructs (Box C) show very tight gene regulation, as indicated by expression levels in the absence of Dox.

Overall, Doxycycline treatment increased viral particle expression, irrespective of the induction system.

Example 4: Generation and Analysis of VSV-G/GagPol Packaging Cell Lines

Figure 6:
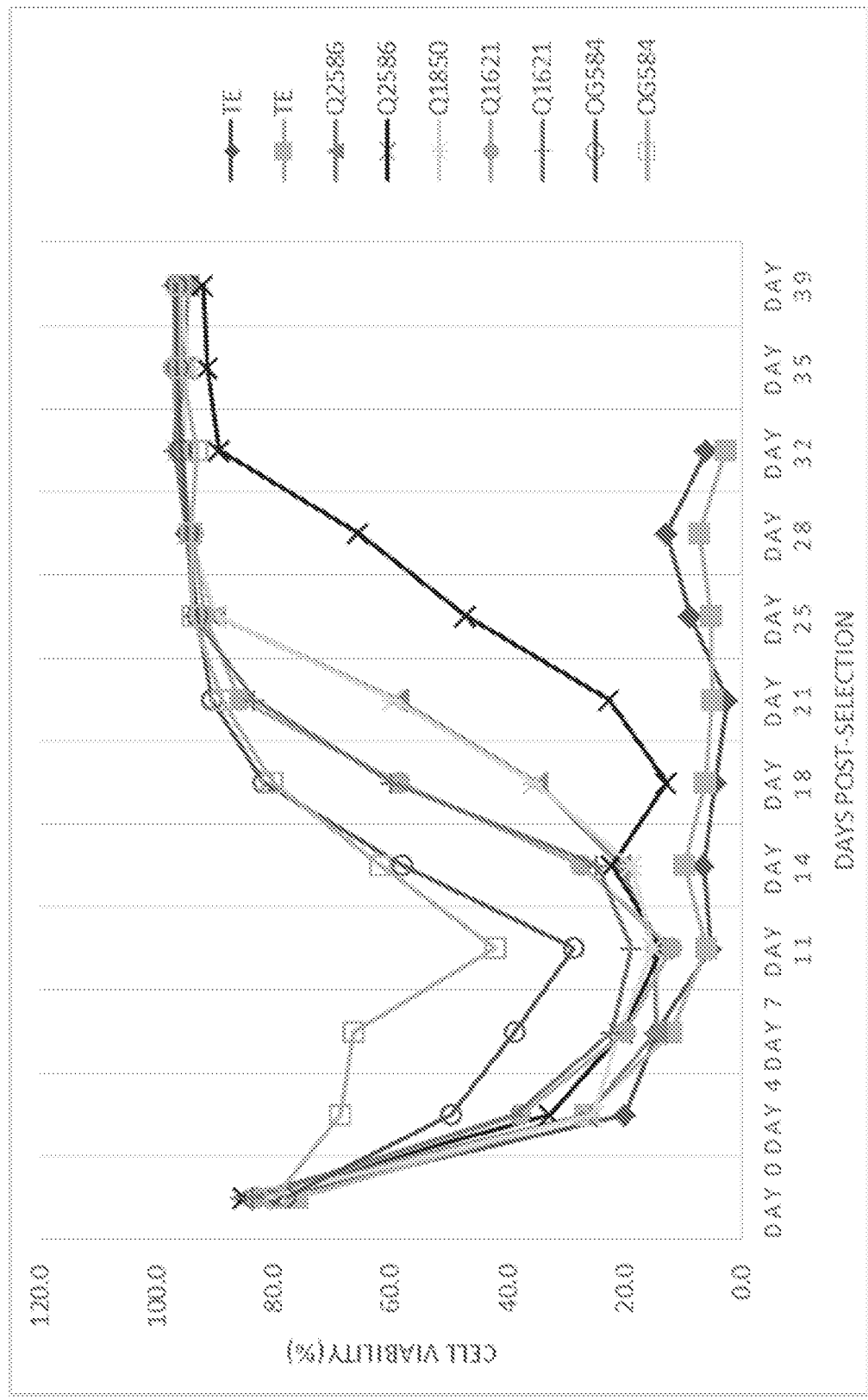
FIG. 6: Viability of the different packaging cell lines during puromycin selection.

Suspension HEK293 cells were transfected with linearized inducible packaging constructs encoding either VSV-G or VSV-G and GagPol with or without apoptosis inhibitors (detailed in Table 2 below) using linear PEI. Subsequently, cells with stably integrated genes were selected for with puromycin treatment until ≥90% viability was obtained with growth characteristics similar to the host cell line (FIG. 1). The VSV-G/GagPol cell pools were carried forward to single cell cloning to obtain a monoclonal high expressing cell line. This was performed via single cell sorting using the Sony SH800 Cell Sorter into prepared cloning media in 96 well plates. Single cells forming colonies were then taken through several scale-up stages until sufficient numbers of cells were obtained for VSV-G protein expression assessment. For this purpose, cell clones were incubated with either vehicle control (DMSO) or Doxycycline for 24 hours to induce VSV-G/GagPol expression. The cells were stained with anti-VSV-G and corresponding secondary FITC-conjugated antibody and analysed by flow cytometry for FITC positive cells. The results are shown in FIG. 6.

TABLE 2

Constructs used in stable packaging cell line generation

| Plasmid | Description | Apoptosis inhibitor | Constitutive/ Inducible |
|---|---|---|---|
| Q2586 | Inducible VSVG with promoter(EF1a)-Puro + EBNA5 cassette | EBNA5 | Inducible |
| Q1850 | Inducible VSVG & GagPol with promoter(EF1a)-Puro + IAP1/EBNA5 cassettes | IAP1 EBNA5 | Inducible |
| Q1621 | Inducible VSVG & GagPol with promoter(EF1a)-Puro | | Inducible |
| OG584 | CMV-Puromycin | | |

Figure 7:
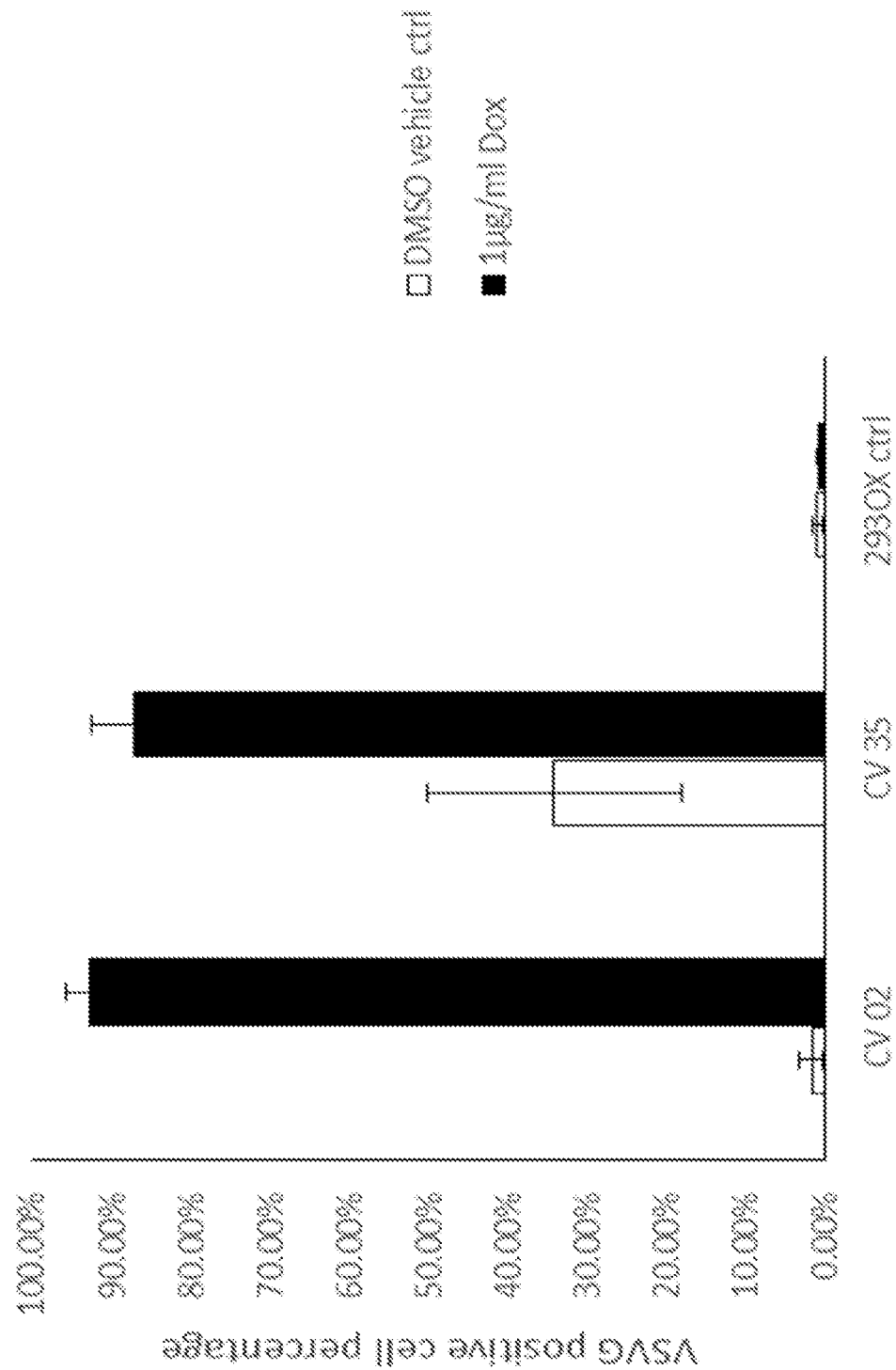
FIG. 7: Surface VSV-G expression following induction in identified clones of interest as assessed by % FITC positive population.

A large number of clonal cell lines were produced following cloning experiments. Representative data from two clones is shown in FIG. 7. Both clone CV02 and CV 35 showed high level expression of VSV-G following doxycycline treatment. However, CV 35 also showed high basal expression of VSV-G, indicating leaky-functionality of the Tet regulation system. This demonstrates that using the generated packaging constructs, stable high expression of VSV-G/GagPol genes can be achieved in the inducible context.

Example 5: Generation and Analysis of Producer Cell Lines

Monoclonal VSV-G/GagPol suspension HEK293 cell lines (as detailed in Example 4) are transfected with linearized constitutive constructs encoding either Rev only or a combination of Rev and viral genome (eGFP or CD19) using linear PEI (see Table 3 for construct details). Subsequently, cells with stably integrated genes are selected for with blasticidin selection until 90% viability is obtained with growth characteristics similar to the host cell line. The generated producer cells are induced with Doxycycline, the culture supernatant collected after a set production period and clarified from cell debris. Subsequently, this viral supernatant is serially diluted and used for infection of Jurkat cells (eGFP and CD19) or adherent 293 cells (eGFP only) for 72 hours. Jurkat and 293 cells infected with eGFP lentivirus are directly analysed via flow cytometry, whereby the dilution yielding 10-20% eGFP positive (i.e. transduced) cells is used to calculate the infectious particle concentration.

In the instance of CD19, infected Jurkat cells are stained via protein L to detect surface CD19 expression and similarly to eGFP, infectious particle concentrations are estimated. The packaging cell line (VSV-G/GagPol+Rev) is evaluated using simultaneous Doxycycline induction of VSV-G/GagPol expression and transient transfection of eGFP virus genome. The produced viral supernatant is then serially diluted and used to infect Jurkat and 293 cells to establish infectious particle concentrations. The preferred producer pools are taken forward to single cell sorting using the Sony SH800 Cell Sorter into prepared cloning media in 96 well plates. Single cells forming colonies are then taken through several scale-up stages until sufficient numbers of cells are obtained for assessing lentivirus production following doxycycline induction in a manner outlined above.

TABLE 3

Constructs used for transfection of the monoclonal packaging cell line for stable producer cell line generation

| Plasmids | Description | Constitutive/Inducible |
|---|---|---|
| Q3928 | pSF-nano-lenti-genome-SFFV-eGFP-RSV-Rev-PGK-Blast | Constitutive |
| Q3931 | pSF-nano-lenti-genome-SFFV-CD19-CAR-ORIG-RSV-Rev-PGK-Blast | Constitutive |
| Q3939 | pSF-core-RSV-Rev-PGK-Blast-KanR | Constitutive |
| OG588 | pSF-CMV-Blast | Constitutive |

Example 6: Analysis of Transcriptional Read Through Between Viral Genes and Potential to Generate Replication Competent Lentivirus (RCL)

A major safety implication with the use of retroviral vectors is the risk of generating replication-competent particles. This has been addressed in the context of transient Lentivirus expression by third generation systems, which incorporate separate vectors for the packaging factors, as well as a deletion within the LTR regions to ablate promoter activity, making transcription of the transgene dependent on an internal promoter.

Figure 8:
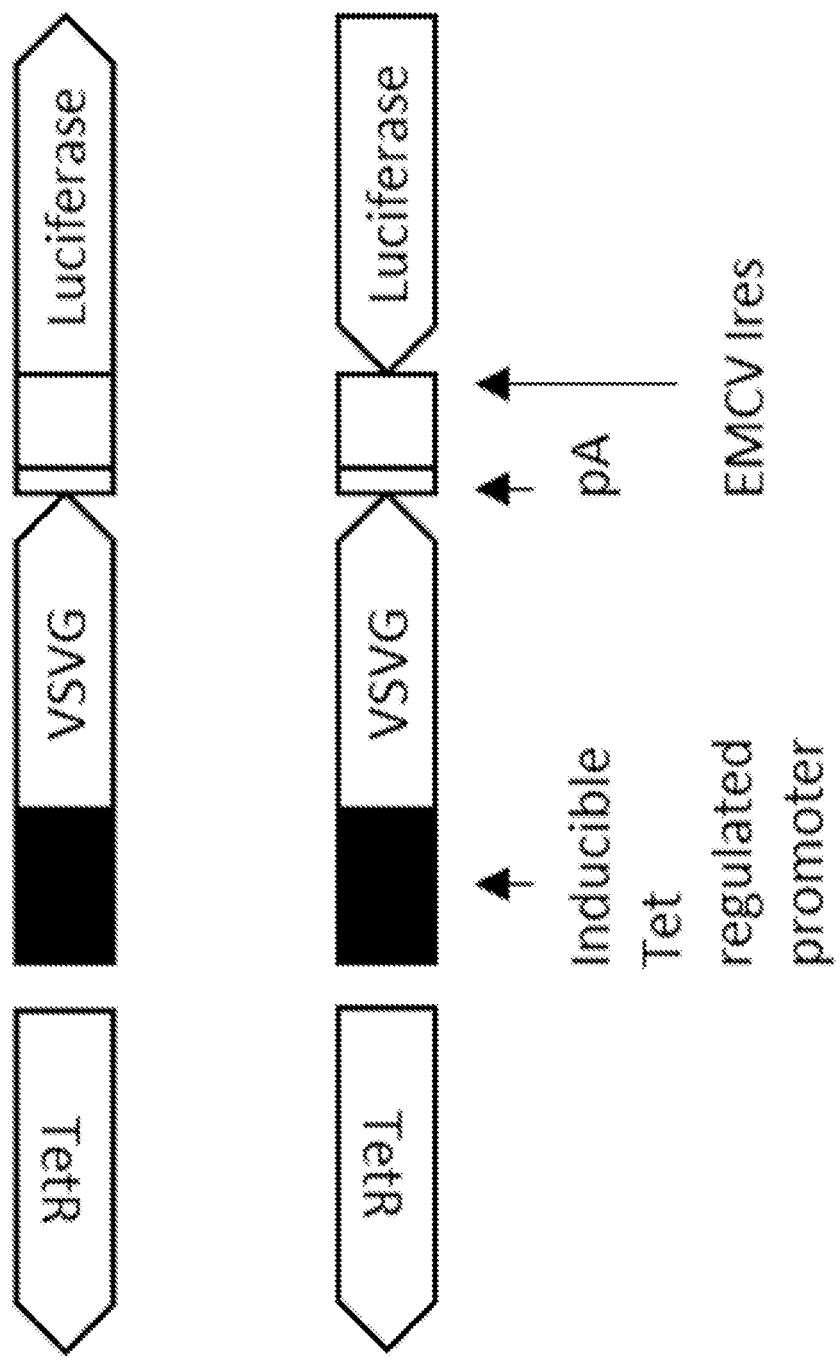
FIG. 8: VSV-G expression constructs for transcriptional read-through assessment.

To assess the configuration of the VSV-G and gag-pol genes in the constructs used to generate the stable bioproduction cell lines, and its potential to reduce risk of RCL generation, two additional constructs were generated where VSV-G was expressed in tandem with a Luciferase reporter, in both forward and reverse orientations. This is illustrated in FIG. 8.

The two constructs were subsequently transiently transfected into adherent HEK293T cells, treated with Doxycycline to induce transcription, and luciferase activity assayed after 24 hrs. Presence of luciferase activity in the forward orientation construct is indicative of read-through transcription, which directly relates to safety concerns that are avoided by the gene configuration used in this invention in stable cell line context.

Example 7: Analysis of VSV-G/GagPol Packaging Cell Lines

Additional packaging cell lines were produced by identical methods to those described in Example 4. Packaging cell lines were grown in both shake flask and in miniature bioreactors systems (AMBR15), in order to analyse and optimise production parameters. Those illustrated here were produced by stable integration of the linearised Q1850 plasmid.

Figure 9:
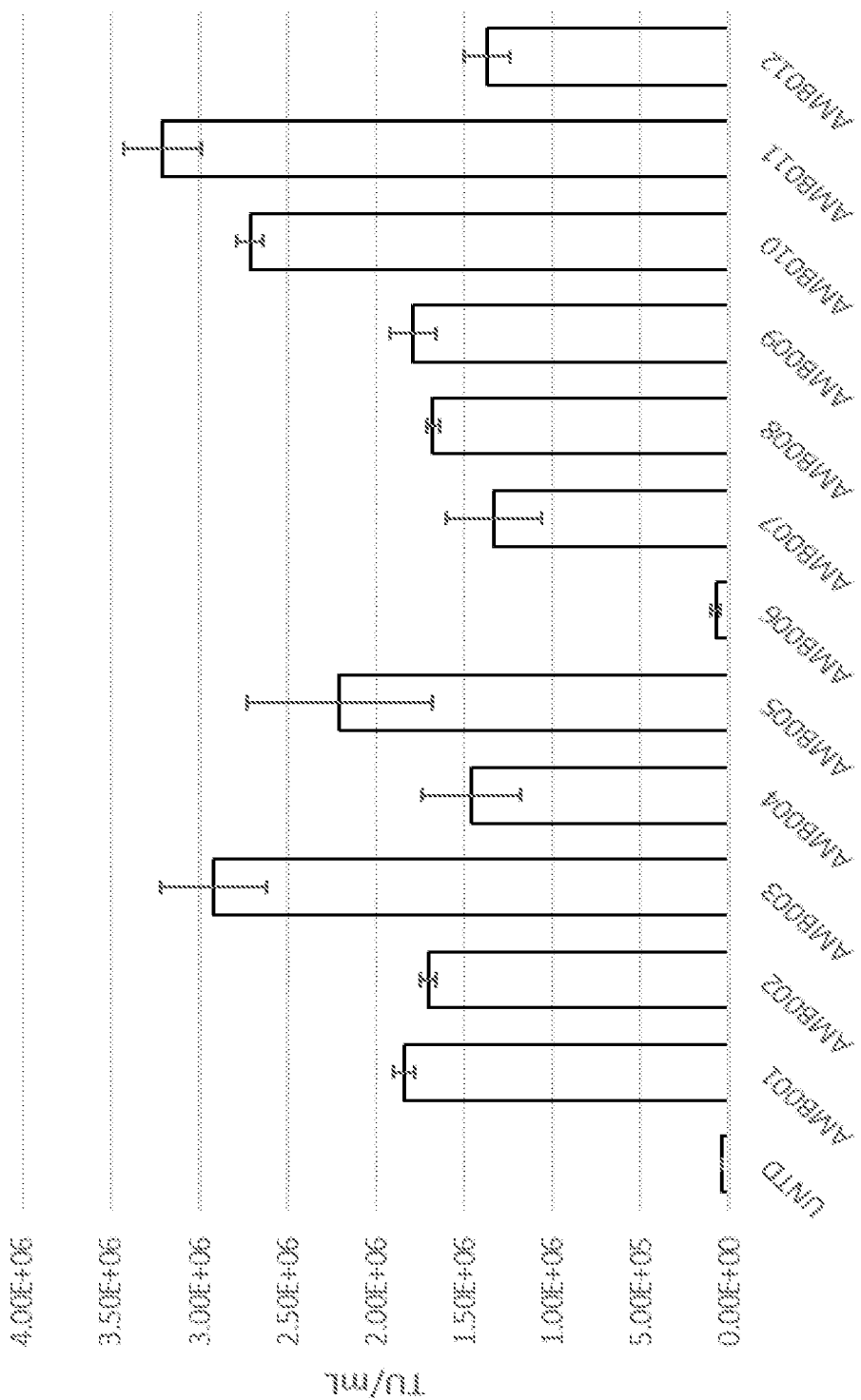
FIG. 9: Analysis of the preferred packaging line (CV170) using different process conditions in the AMBR bioreactor system.

To investigate production parameters, packaging cell lines were cultured for 72 hrs after PEI-based transfection of Rev/Genome plasmid (Q1847) and induced using doxycycline. Supernatants were collected and analysed by flow cytometry-based infectious titre assay. Data is presented in FIG. 9, and represents analysis of the preferred packaging line (CV170) using different process conditions in the AMBR bioreactor system.

Example 8: Analysis of Producer Cell Lines

The preferred packaging cell line (CV170) was used as the starting point for generation of the fully stable producer cell line. A stable pool was created by stable integration of the linearised Q3928 plasmid, and then cloned by FACS sorting. Clonal lines were then expanded and analysed in deep well shaking plates. Based on this data, selected clonal cell lines were scaled-up into shake flask culture.

Figure 10:
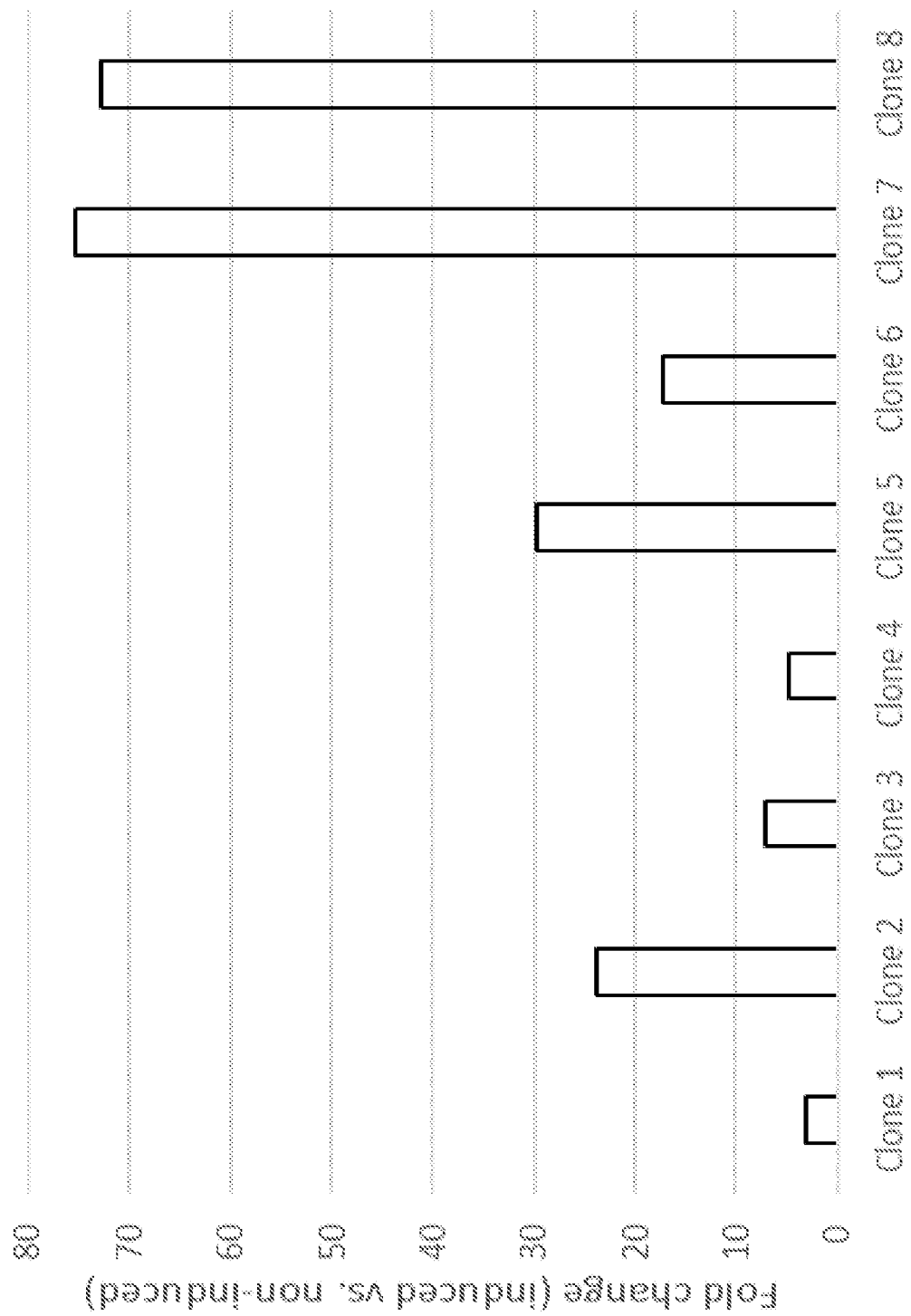
FIG. 10: Fold change in viral titre from un-induced to induced producer cell lines.

Once transferred into shake flask, producer cell lines were induced by addition of doxycycline to the cell culture media. 72 hrs post-induction, supernatants were collected and analysed by flow cytometry-based infectious titre assay. Data is presented in FIG. 10 as fold change in viral titre from un-induced to induced.

SEQUENCES

SEQ ID NO: 1-HIV-1 env nucleotide
ATGAGAGTGAAGGAGAAATATCAGCACTTGTGGAGATGGGGGTGGAGAT
GGGGCACCATGCTCCTTGGGATGTTGATGATCTGTAGTGCTACAGAAAA
ATTGTGGGTCACAGTCTATTATGGGGTACCTGTGTGGAAGGAAGCAACC
ACCACTCTATTTTGTGCATCAGATGCTAAAGCATATGATACAGAGGTAC
ATAATGTTTGGGCCACACATGCCTGTGTACCCACAGACCCCAACCCACA
AGAAGTAGTATTGGTAAATGTGACAGAAAATTTTAACATGTGGAAAAAT
GACATGGTAGAACAGATGCATGAGGATATAATCAGTTTATGGGATCAAA
GCCTAAAGCCATGTGTAAAATTAACCCCACTCTGTGTTAGTTTAAAGTG
CACTGATTTGAAGAATGATACTAATACCAATAGTAGTAGCGGGAGAATG
ATAATGGAGAAAGGAGAGATAAAAAACTGCTCTTTCAATATCAGCACAA
GCATAAGAGGTAAGGTGCAGAAAGAATATGCATTTTTTTATAAACTTGA
TATAATACCAATAGATAATGATACTACCAGCTATAAGTTGACAAGTTGT
AACACCTCAGTCATTACACAGGCCTGTCCAAAGGTATCCTTTGAGCCAA
TTCCCATACATTATTGTGCCCCGGCTGGTTTTGCGATTCTAAAATGTAA

SEQUENCES

```
TAATAAGACGTTCAATGGAACAGGACCATGTACAAATGTCAGCACAGTA
CAATGTACACATGGAATTAGGCCAGTAGTATCAACTCAACTGCTGTTAA
ATGGCAGTCTAGCAGAAGAAGAGGTAGTAATTAGATCTGTCAATTTCAC
GGACAATGCTAAAACCATAATAGTACAGCTGAACACATCTGTAGAAATT
AATTGTACAAGACCCAACAACAATACAAGAAAAGAATCCGTATCCAGA
GAGGACCAGGGAGAGCATTTGTTACAATAGGAAAAATAGGAAATATGAG
ACAAGCACATTGTAACATTAGTAGAGCAAAATGGAATAACACTTTAAAA
CAGATAGCTAGCAAATTAAGAGAACAATTTGGAAATAATAAAACAATAA
TCTTTAAGCAATCCTCAGGAGGGGACCCAGAAATTGTAACGCACAGTTT
TAATTGTGGAGGGGAATTTTTCTACTGTAATTCAACACAACTGTTTAAT
AGTACTTGGTTTAATAGTACTTGGAGTACTGAAGGGTCAAATAACACTG
AAGGAAGTGACACAATCACCCTCCCATGCAGAATAAAACAAATTATAAA
CATGTGGCAGAAAGTAGGAAAAGCAATGTATGCCCCTCCCATCAGTGGA
CAAATTAGATGTTCATCAAATATTACAGGGCTGCTATTAACAAGAGATG
GTGGTAATAGCAACAATGAGTCCGAGATCTTCAGACCTGGAGGAGGAGA
TATGAGGGACAATTGGAGAAGTGAATTATATAAATATAAAGTAGTAAAA
ATTGAACCATTAGGAGTAGCACCCACCAAGGCAAAGAGAAGAGTGGTGC
AGAGAGAAAAAAGAGCAGTGGGAATAGGAGCTTTGTTCCTTGGGTTCTT
GGGAGCAGCAGGAAGCACTATGGGCGCAGCCTCAATGACGCTGACGGTA
CAGGCCAGACAATTATTGTCTGGTATAGTGCAGCAGCAGAACAATTTGC
TGAGGGCTATTGAGGCGCAACAGCATCTGTTGCAACTCACAGTCTGGGG
CATCAAGCAGCTCCAGGCAAGAATCCTGGCTGTGGAAAGATACCTAAAG
GATCAACAGCTCCTGGGGATTTGGGGTTGCTCTGGAAAACTCATTTGCA
CCACTGCTGTGCCTTGGAATGCTAGTTGGAGTAATAAATCTCTGGAACA
GATTTGGAATCACACGACCTGGATGGAGTGGGACAGAGAAATTAACAAT
TACACAAGCTTAATACACTCCTTAATTGAAGAATCGCAAAACCAGCAAG
AAAAGAATGAACAAGAATTATTGGAATTAGATAAATGGGCAAGTTTGTG
GAATTGGTTTAACATAACAAATTGGCTGTGGTATATAAAATTATTCATA
ATGATAGTAGGAGGCTTGGTAGGTTTAAGAATAGTTTTTGCTGTACTTT
CTATAGTGAATAGAGTTAGGCAGGGATATTCACCATTATCGTTTCAGAC
CCACCTCCCAACCCCGAGGGGACCCGACAGGCCCGAAGGAATAGAAGAA
GAAGGTGGAGAGAGAGACAGAGACAGATCCATTCGATTAGTGAACGAT
CCTTGGCACTTATCTGGGACGATCTGCGGAGCCTGTGCCTCTTCAGCTA
CCACCGCTTGAGAGACTTACTCTTGATTGTAACGAGGATTGTGGAACTT
CTGGGACGCAGGGGGTGGGAAGCCCTCAAATATTGGTGGAATCTCCTAC
AGTATTGGAGTCAGGAACTAAAGAATAGTGCTGTTAGCTTGCTCAATGC
CACAGCCATAGCAGTAGCTGAGGGGACAATAGGGTTATAGAAGTAGTA
CAAGGAGCTTGTAGAGCTATTCGCCACATACCTAGAAGAATAAGACAGG
GCTTGGAAAGGATTTTGCTATAA
```

SEQ ID NO: 2-HIV-1 Env amino acid
MRVKEKYQHLWRWGWRWGTMLLGMLMICSATEKLWVTVYYGVPVWKEAT
TTLFCASDAKAYDTEVHNVWATHACVPTDPNPQEVVLVNVTENFNMWKN
DMVEQMHEDIISLWDQSLKPCVKLTPLCVSLKCTDLKNDTNTNSSSGRM
IMEKGEIKNCSFNISTSIRGKVQKEYAFFYKLDIIPIDNDTTSYKLTSC
NTSVITQACPKVSFEPIPIHYCAPAGFAILKCNNKTFNGTGPCTNVSTV
QCTHGIRPVVSTQLLLNGSLAEEEVVIRSVNFTDNAKTIIVQLNTSVEI
NCTRPNNNTRKRIRIQRGPGRAFVTIGKIGNMRQAHCNISRAKWNNTLK
QIASKLREQFGNNKTIIFKQSSGGDPEIVTHSFNCGGEFFYCNSTQLFN
STWFNSTWSTEGSNNTEGSDTITLPCRIKQIINMWQKVGKAMYAPPISG
QIRCSSNITGLLLTRDGGNSNNESEIFRPGGGDMRDNWRSELYKYKVVK
IEPLGVAPTKAKRRVVQREKRAVGIGALFLGELGAAGSTMGAASMTLTV
QARQLLSGIVQQQNNLLRAIEAQQHLLQLTVWGIKQLQARILAVERYLK
DQQLLGIWGCSGKLICTTAVPWNASWSNKSLEQIWNHTTWMEWDREINN
YTSLIHSLIEESQNQQEKNEQELLELDKWASLWNWFNITNWLWYIKLFI
MIVGGLVGLRIVFAVLSIVNRVRQGYSPLSFQTHLPTPRGPDRPEGIEE
EGGERDRDRSIRLVNGSLALIWDDLRSLCLFSYHRLRDLLLIVTRIVEL
LGRRGWEALKYWWNLLQYWSQELKNSAVSLLNATAIAVAEGTDRVIEVV
QGACRAIRHIPRRIRQGLERILL SEQ ID NO: 3-VSV-G nucleotide
```
atgaagtgtctgctgtacctggcgttcctgtttatcggggtgaactgca
agttcactatcgtgtttccgcacaaccaaaagggcaactggaaaaacgt
gccttcaaattaccattattgcccagcagctcggacctgaactggcac
aatgacctcattggaaccgcgctgcaggtgaagatgccaaagagccaca
aggctatccaggctgacggatggatgtgccacgcgtcaaatgggtgac
tacctgcgatttccgctgtacggaccaaaatacatcacgcacagcatc
agatcattcaccccgtcagtggaacaatgcaaagaatccatcgaacaga
ctaagcagggaacctggctgaaccctggatttccgccgcagtcgtgtgg
gtacgcaaccgtgaccgatgcagaggccgtgatcgtgcaagtcacgccg
catcacgtgcttgtggacgagtacaccggagaatgggtcgattcccgt
tcatcaacggcaaggtgtccaactacatttgcccaaccgtgcacaacag
cactacttggcacagcgactacaaagtgaaggtctgtgtgattccaac
ctgatctccatggatatcacttttcttctcggaagacggcgaactgtcct
cactgggcaaagaaggaactgggtttcgctcaaattacttcgcctacga
aactggaggaaaagcctgcaagatgcagtactgcaagcactgggcgtg
agactaccccagcggtgtctggttcgagatggccgataaggaccgtgttg
```
```
cagcagcgagattcccggaatgccctgagggatcgagcatctccgctcc
aagccaaacttcagtggacgtgagcctgatccaggacgtggaacggatt
ctcgactactcgctgtgccaggagacctggtcgaagatcagagcgggac
tgcccatctcaccggtggacctgtcctacctggcgccaaagaatccggg
cactggaccggcgttcaccatcatcaacggcaccctcaaatacttcgag
acgcggtacatccgggtggacatcgcagctccgatcctctcccggatgg
tgggaatgatctcggggactactaccgaacgcgagctctgggacgactg
ggcaccttacgaggatgtcgagatcggacctaacggagtgctccggacc
tcctccgggtacaagttccctctgtacatgatcggccatggcatgctgg
actcggatctgcatctgtcgtccaaagcacaggtgtttgaacacccaca
cattcaagacgccgccagccagctgccggacgatgagtcgctgttcttc
ggagacacgggcttgtcaaagaatccatcgagctggtggaaggatggt
tttcatcctggaaaagcagcatcgcttcattcttcttcatcattggcct
gatcatcggcctatttctagtcctgcgggtgggaattcatctgtgcatc
aagctcaagcacactaagaagcggcaaatctacactgatatcgagatga
atcgcctgggcaag
```

SEQ ID NO: 4-VSV-G amino acid
MKCLLYLAFLFIGVNCKFTIVFPHNQKGNWKNVPSNYHYCPSSSDLNWH
NDLIGTALQVKMPKSHKAIQADGWMCHASKWVITCDFRWYGPKYITHSI
RSFIPSVEQCKESIEQTKQGTWLNPGFPPQSCGYATVIDAEAVIVQVIP
HHVLVDEYTGEWVDSQFINGKCSNYICPTVHNSTTWHSDYKVKGLCDSN
LISMDITFFSEDGELSSLGKEGIGFRSNYFAYETGGKACKMQYCKHWGV
RLPSGVWFEMADKDLFAAARFPECPEGSSISAPSQTSVDVSLIQDVSTI
LDYSLCQETWSKIRAGLPISPVDLSYLAPKNPGIGPAFTIINGILKYFE
TRYIRVDIAAPILSRMVGMISGITTERELWDDWAPYEDVEIGPNGVLRI
SSGYKFPLYMIGHGMLDSDLHLSSKAQVFEHPHIQDAASQLPDDESLFF
GDTGLSKNPIELVEGWFSSWKSSIASFFFIIGLIIGLFLVLRVGIHLCI
KLKHIKKRQIYIDIEMNRLGK SEQ ID NO: 5-HIV-1 gag-pol nucleotide
```
atgggtgcgagagcgtcagtattaagcggcggagaattagatcgatggg
aaaaaattcggttaaggccagggggaagaaaaaatataaattaaaaca
tatagtatgggcaagcagggagctagaacgattcgcagttaatcctggc
ctgttagaaacatcagaaggctgtagacaaatactgggacagctacaac
catcccttcagacaggatcagaagaacttagatcattatataataacagt
agcaaccctctattgtgtgcatcaaaggatagagatataaaagacaccaag
gaagctttagacaagatagaggaagagcaaaacaaaagtaagaaaaaag
cacagcaagcagcagctgacacaggacacagcaatcaggtcagccaaaa
ttaccctatagtgcagaacatccaggggcaaatggtacatcaggccata
tcacctagaactttaaatgcatgggtaaaagtagtagaagagaaggctt
tcagcccagaagtgatacccatgtttttcagcattatcagaaggagccac
cccacaagatttaaacaccatgctaaacacagtgggggggacatcaagca
gccatgcaaatgttaaaagagaccatcaatgaggaagctgcagaatggg
atagagtgcatccagtgcatgcagggcctattgcaccaggccagatgag
agaaccaaggggaagtgacatagcaggaactactagtacccttcaggaa
caaataggatggatgacacataatccacctatcccagtaggagaaatct
ataaagatggataatcctgggattaaataaaatagtaagaatgtatag
ccctaccagcattctggacataagacaaggaccaaaggaaccctttaga
gactatgtagaccggttctataaaactctaagagccgagcaagcttcac
aagaggtaaaaaattggatgacagaaaccttgttggtccaaaatgcgaa
cccagattgtaagactattttaaaagcattgggaccaggagcgacacta
gaagaaatgatgacagcatgtcagggagtgggggggacccggccataag
caagattttggctgaagcaatgagccaagtaacaaatccagctaccat
aatgatacagaaaggcaattttaggaaccaaagaaagactgttaagtgt
ttcaattgtggcaaagaagggcacatagccaaaaattgcagggccccta
ggaaaaagggctgttggaaatgtggaaaggaaggacaccaaatgaaaga
ttgtactgagagacaggctaattttttagggaagatctggccttcccac
aagggaaggccagggaattttcttcagagcagaccagagccaacagccc
caccagaagagagcttcaggtttggggaagagacaacaactccctctca
gaagcaggagccgatagacaaggaactgtatcctttagcttccctcaga
tcactctttggcagcgaccctcgtcacaataaagataggggggaatt
aaaggaagctctattagatacaggagcagatgatacagtattagaagaa
atgaatttgccaggaagatggaaaccaaaaatgatagggggaattggag
gttttatcaaagtaagacagtatgatcagatactcatagaaatctgcgg
acataaagctataggtacagtattagtaggacctacacctgtcaacata
attggaagaaatctgttgactcagattggctgcacttaaattttccca
ttagtcctattgagactgtaccagtaaaattaaagccaggaatggatgg
cccaaaagttaaacaatggccattgacagaagaaaaaataaaagcatta
gtagaaatttgtacagaaatggaaaggaaggaaaaatttcaaaaattg
ggcctgaaaatccatacaatactccagtatttgccataaagaaaaaaga
cagtactaaatggagaaaattagtagatttcagagaacttaataagaga
actcaagacttctgggaagttcaattaggaataccacatcctgcagggt
taaaacagaaaaaatcagtaacagtactggatgtgggcgatgcatattt
ttcagttcccttagataaagacttcaggaagtatactgcatttaccata
cctagtataaacaatgagacaccagggattagatatcagtacaatgtgc
ttccacagggatggaaaggatcaccagcaatattccagtgtagcatgac
``` aaaaatcttagagccttttagaaaacaaaatccagacatagtcatctat
caatacatggatgatttgtatgtaggatctgacttagaaatagggcagc
atagaacaaaaatagaggaactgagacaacatctgttgaggtgggggatt
taccacaccagacaaaaaacatcagaaagaacctccattcctttggatg
ggttatgaactccatcctgataaatggacagtacagcctatagtgctgc
cagaaaaggacagctggactgtcaatgacatacagaaattagtgggaaa
attgaattgggcaagtcagatttatgcagggattaaagtaaggcaatta
tgtaaacttcttagggaaccaaagcactaacagaagtagtaccactaa
cagaagaagcagagctagaactggcagaaaacagggagattctaaaaga
accggtacatggagtgtattatgacccatcaaaagacttaatagcagaa
atacagaagcaggggcaaggccaatggacatatcaaatttatcaagagc
catttaaaaatctgaaaacaggaaagtatgcaagaatgaagggtgccca
cactaatgatgtgaaacaattaacagaggcagtacaaaaaatagccaca
gaaagcatagtaatatggggaaagactcctaaatttaaattacccatac
aaaaggaaacatgggaagcatggtggacagagtattggcaagccacctg
gattcctgagtgggagtttgtcaatacccctcccttagtgaagttatgg
taccagttagagaaagaacccataataggagcagaaacttctatgtag
atggggcagccaatagggaaactaaattaggaaaagcaggatatgtaac
tgacagaggaagacaaaaagttgtcccctaacggacacaacaaatcag
aagactgagttacaagcaattcatctagctttgcaggattcgggattag
aagtaaacatagtgacagactcacaatatgcattgggaatcattcaagc
acaaccagataagagtgaatcagagttagtcagtcaaataatagagcag
ttaataaaaaaggaaaagtctacctggcatgggtaccagcacaaag
gaattggaggaaatgaacaagtagataaattggtcagtgctgaatcag
gaaagtactattttttagatggaatagataaggcccaagaagaacatgag
aaatatcacagtaattggagagcaatggctagtgattttaacctaccac
ctgtagtagcaaaagaaatagtagccagctgtgataaatgtcagctaaa
aggggaagccatgcatggacaagtagactgtagcccaggaatatggca
ctagattgtacacatttagaagaaaagttatcttggtagcagttcatg
tagccagtggatatatagaagcagaagtaattccagcagagacagggca
agaaacagcatacttcctcttaaaattagcaggaagatggccagtaaaa
acagtacatacagacaatggcagcaatttcaccagtactacagttaagg
ccgcctgttggtgggcgggatcaagcaggaatttggcattccctacaa
tccccaaagtcaaggagtaatagaatctatgaataaagaattaaagaaa
attataggacaggtaagagatcaggctgaacatcttaagacagcagtac
aaatggcagtattcatccacaattttaaaagaaaaggggggattgggg
gtacagtgcaggggaaagaatagtagacataatagcaacagacataca
actaaagaattacaaaaacaaattacaaaaattcaaaattttcgggttt
attacagggacagcagagatccagtttggaaaggaccagcaaagctcct
ctggaaaggtgaaggggcagtagtaatacaagataatagtgacataaaa
gtagtgccaagaagaaaagcaaagatcatcagggattatggaaaacaga
tggcaggtgatgattgtgtgcaagtagacaggatgaggattaa SEQ ID NO: 6-HIV-1 rev nucleotide
ATGGCAGGCCGCTCAGGGGACTCGGATGAGGATCTGCTGAAGGCGGTGC
GGCTCATCAAATTCCTGTACCAGAGCAACCCGCCACCGAACCCCGAAGG
AACTCGCCAGGCTCGCAGGAACCGCCGCAGACGCTGGCGCGAACGGCAG
CGCCAGATCCACAGCATCAGCGAACGCATCCTGTCAACTTACTTGGGAC
GGTCAGCGGAACCTGTCCCGCTGCAGCTGCCGCCGCTGGAGCGCCTGAC
TCTGGATTGCAACGAAGACTGCGGAACCAGCGGAACCCAGGGCGTGGGA
AGCCCACAGATCCTGGTGGAATCGCCTACCATCTTGGAAAGCGGCGCGA
AAGAA SEQ ID NO: 7-HIV-1 Rev amino acid
MAGRSGDSDEDLLKAVRLIKFLYQSNPPPNPEGTRQARRNRRRWRERQ
RQIHSISERILSTYLGRSAEPVPLQLPPLERLTLDCNEDCGTSGTQGVG
SPQILVESPTILESGAKE SEQ ID NO: 8-TetR binding site
tccctatcagtgatagaga SEQ ID NO: 9-nucleotide sequence of the TetR
protein
Atgtcgcgcctggacaaaagcaaagtgattaactcagcgctggaactgt
tgaatgaggtgggaattgaaggactcactactcgcaagctggcacagaa
gctgggcgtcgagcagccaacgctgtactggcatgtgaagaataaacgg
gcgctcctagacgcgcttgccatcgaaatgctggaccgccatcacaccc
acttttgccccctggaggcgaatcctggcaagattttctgcgaaacac
tgcaaagtcgttccggtgcgctctgctgtcccaccgcgatggcgcaaaa
gtgcacctgggcactcggcccaccgagaaacaatacgaaccctggaaa
accaactggctttcctttgccaacagggattttcactggagaatgccct
gtacgcactatccgcggtcgggccacttaccctggcgtgcgtcctcgaa
gatcaggagcaccaagtcgccaaggaggaaagagaaactcctaccactg
actcaatgcctccgctcctgagacaagccatcgagctgttcgaccacca
gggtgctgaacctgcatttctgttcgggcttgaactgattatctgcggc
ctggagaaacagttgaagtgcgagtcgggatcctag SEQ ID NO: 10-amino acid sequence of the TetR
protein
MSRLDKSKVINSALELLNEVGIEGLTTRKLAQKLGVEQPTLYWHVKNKR
ALLDALAIEMLDRHHTHFCPLEGESWQDFLRNNAKSFRCALLSHRDGAK
VHLGTRPTEKQYETLENQLAFLCQQGFSLENALYALSAVGHFTLGCVLE
DQEHQVAKEERETPTTDSMPPLLRQAIELFDHQGAEPAFLFGLELIICG
LEKQLKCESGS SEQ ID NO: 11 Apoptosis Inhibitor IAP1
ATGAACGAGGACACTCCGCCGTTTTATTTTATCAATACGCGCGACAACT
TTCGCGATAACATCGCCGAACACGTATTCGATATGTTACTAGAAAGACA
TGGCTCGTTTGAAAATTATCCCATTGTAAACACGGCATTCATCAACAGC
TTGATCGTTAACGGGTTTAAATACAATCAAGTCGATGACCACGTTGTGT
GCGAGTATTGTGAAGCAGAAATAAAAAATTGGTCCGAAGACGAGTGTAT
TGAATATGCACACGTAACCTTGTCGCCGTATTGCGCCTACGCCAATAAG
ATTGCTGAGCATGAATCGTTTGGCGACAACATTACCATCAACGCTGTAC
TGGTAAAAGAAGGCAGACCCAAGTGTGTGTACAGATGCATGTCCAATTT
ACAGTCGCGTATGGATACGTTTGTTACTTTTTGGCCTGCCGCATTGCGT
GACATGATTATAAACATCGCGGAAGCGGGACTTTTTTACACGGGTCGCG
GAGACGAAACTGTATGTTTCTTTTGCGATTGTTGCGTACGTGATTGGCA
TACTAACGAAGACGCCTGGCAGCGACACGCCACCGAAAACCCGCAATGC
TACTTTGTGCTGTCGGTGAAAGGTAAAGAATTTTGTCAAAACGCAATTA
CTGCCACTCACGTTGATAAACGTGACGATGACGACGACGACGATGATAA
TTTAAACGAACGATCGTGATGACATTGAGGAAAAATACGAATGCAAAGTC
TGTCTTGAACGCCAACGCGACGCAGTGCTTATGCCTTGTCGGCATTTTT
GTGTTTGCGTTCAGTGTTATTTTGGTTTAGATCAAAAGTGTCCGACCTG
TCGTCAAGACGTCACCGATTTCATAAAAATATTTGTGGTGTAG SEQ ID NO: 12-Apoptosis Inhibitor EBNA5
ATGGGAGATCGTAGCGAAGTCCCCGGTCCGGCACGCCCCGGACCTCCGG
GAATTGGCCCCGAAGGCCCTCTAGGACAGCTCCTGCGTCGGCACCGCAG
TCCCTCCCCGACCCGTGGAGGCCAAGAGCCCCGGCGGGTCAGACGCCGC
GTATTAGTCCAGCAGGAAGGAGGAAGTAGTAAGTGGCTCACCATCAGGGC
CCCGGGGAGACAGGTCAGAGGTCCCAGGCCCAGCCCGCCCTGGCCCGCC
GGGTATCGGACCCGAAGGGCCCCTGGGCCAGCTGTTGCGCCGGCACAGA
TCACCCAGCCCCACCCGCGGCGGTCAGGAACCTCGCCGGGTCAGACGGC
GGGTGCTCGTACAACAGGAAGAGGAAGTTGTTTCTGGATCGCCCTCGGG
CCCGCGCGGCGACCGCTCAGAGGTGCCTGGACCAGCCCGGCCTGGGCCC
CCCGGAATCGGACCTGAAGGACCGCTGGGTCAGTTACTACGCCGGCACC
GGTCCCCTTCGCCGACTCGGGGCGGGCAGGAACCCCGGCGCGTGAGGCG
TCGCGTCCTGGTCCAGCAGGAGGAAGAGGTTGTCAGCGGCAGCCCATCC
GGGCCGAGGGGGATCGTTCGGAAGTGCCCGGCCCAGCACGCCCGGGCC
CGCCAGGTATTGGGCCCGAAGGTCCGTTAGGTCAGCTGCTCCGGCGGCA
TAGGTCACCATCCCCGACTCGGGGCGGCCAGGAACCCGGGAGAGTGCGC
CGGAGAGTGCTGGTGCAACAGGAGGAAGAAGTCGTGTCCGGGTCGCCGT
CAGGTCCTCGGGGCGACCGGTCAGAAGTACCTGGACCGGCCCGCCCCGG
ACCGCCGGGCATCGGGCCGGAAGGCCCCCTGGGACAGCTGCTGCGGAGA
CATAGCTGCCATCCCCCACCAGAGGCGGACAGGAACCGCGCCGCGTGC
GCCGCCGGGTGCTGGTTCAGCAAGAAGAAGAGGTTGTGTCGGGTTCACC
TAGCGGCCCGAGAGGCGACCGGAGCGAAGTGCCAGGACCAGCACGTCCG
GGCCCTCCAGGTATCGGCCCAGAAGGACCACTGGGACAACTGCTGAGAC
GCCATCGCTCGCCGAGCCCTACGCGCGGAGGTCAAGAACCGAGACGGGT
CCGCAGACGAGTCCTCGTTCAACAAGAAGAAGAGGTCGTGTCTGGAAGC
CCGTCTGGCCCAAGAGGGGACAAGAGGGCAGGTTGCCGGCCGGCGCCGG
CGGGGCCGCCGGGGATCGGGCCTGAAGGTCCGCTGGGGCAGCTCTTGCG
CAGACACCGCTCGCCCAGCCCAACCCGCGGTGGACAAGAACCCCGACGG
GTGCGGCGGCGCGTGCTCGTGCAACAAGAAGAAGAGGTTGTCTCGGGCT
CGCCATCTGGCCCGCTCAGACCAAGACCGCGACCGCCGGCCCGGTCCCT
CCGCGAATGGCTGCTGCGCATCAGAGACAGATTCGAGCCGCCAACTGAA
ACCACCCAGCGGCAGTCCATCTACATTGAGGAAGAGGAAGATGAGGATT
AG SEQ ID NO: 13-Apoptosis Inhibitor BCL-XL
ATGAGCCAGTCAAATCGGGAACTGGTGGTGGATTTTCTGAGCTACAAGC
TCTCGCAAAAGGGCTACTCATGGAGCCAGTTTTCGGATGTCGAAGAAAA
CCGGACCGAGGCTCCAGAGGGCACCGAATCGGAGATGGAAACTCCGTCA
GCAATCAACGGAAATCCATCATGGCACCTGGCAGATAGCCCGGCGGTGA
ACGGAGCAACCGGACATTCAAGCTCCCTGGACGCCAGAGAAGTGATTCC
GATGCGGCAGTGGAGCAGGCGCTACGCGAAGCGGGAGACGAGTTCGAG
CTGCGGTACAGGAGAGCTTTTAGCGACCTGACTAGCCAGCTCCACATCA
CTCCGGGGACCGCTACCAGTCGTTTGAACAGGTGGTGAACGAGCTGTT
TCGGGATGGAGTCAACTGGGGCAGAATCGTGGCCTTCTTTTCCTTCGGC
GGTGCGCTGTGCGTCGAATCCGTGGACAAGGAGATGCAGGTCCTGGTCA
GCCGGATCGCAGCGTGGATGGCCACTTATCTCAACGATCACCTGGAGCC
GTGGATTCAAGAGAATGGGGGCTGGGACACCTTCGTGGAACTGTATGGA

| SEQUENCES |
|---|
| AACAACGCGGCAGCAGAGTCGAGGAAGGGCCAAGAACGCTTTAATCGGT |
| GGTTCCTGACTGGAATGACGGTGGCAGGAGTGGTGCTACTGGGCTCGCT |
| TTTCAGCCGCAAATAA |

| SEQUENCES |
|---|
| SEQ ID NO: 14-N-terminal signal peptide from VSV-G |
| MLSYLIFALAVSPILG |

The invention claimed is:

1. A double-stranded nucleic acid molecule comprising:

(a) a first nucleic acid comprising an env gene; and (b) a second nucleic acid comprising a gag-pol gene;

wherein coding sequences of the first and second nucleic acids are on opposing strands of the double-stranded nucleic acid molecule, wherein the env and gag-pol genes are independently operably-associated with first and second inducible promoters, respectively, the first and second promoters having less than 95% nucleotide sequence identity between them, and wherein the double-stranded nucleic acid molecule comprises 1 or more nucleotide sequences encoding apoptosis inhibitors IAP1 and EBNA5.

2. The double-stranded nucleic acid molecule as claimed in claim 1, wherein the nucleotide sequence identity between the first and second promoters is less than 90%, 85%, 80%, 70% or 60%.

3. The double-stranded nucleic acid molecule as claimed in claim 1, wherein the env gene is a VSV-G gene.

4. The double-stranded nucleic acid molecule as claimed in claim 1, wherein the gag-pol gene is from HIV-1, or is a derivative thereof.

5. The double-stranded nucleic acid molecule as claimed in claim 1, wherein the nucleic acid molecule additionally comprises a rev gene.

6. The double-stranded nucleic acid molecule as claimed in claim 1, wherein the nucleic acid molecule additionally comprises a transgene.

7. A retroviral vector comprising a double-stranded nucleic acid molecule as claimed in claim 1.

8. A mammalian cell comprising a double-stranded nucleic acid as claimed in claim 1.

9. A retroviral packaging cell comprising a double-stranded nucleic acid molecule as claimed in claim 1.

10. A kit comprising:

(i) a retroviral packaging vector comprising a double-stranded nucleic acid molecule as claimed in claim 1;

together with one or more of the following:

(ii) a retroviral Transfer Vector comprising a transgene and a retroviral rev gene;

(iii) cells of a cell line suitable for the production of virus particles.

11. A kit comprising:

(i) a retroviral packaging vector comprising a double-stranded nucleic acid molecule as claimed in claim 1 which additionally comprises a rev gene;

together with one or more of the following:

(ii) a retroviral Transfer Vector comprising a transgene;

(iii) cells of a cell line suitable for the production of virus particles.

12. A process for producing a retroviral packaging cell, the process comprising the steps:

(i) stably integrating a double-stranded nucleic acid molecule as claimed in claim 1 into a mammalian cell, thereby producing a mammalian cell that expresses retroviral env and gag-pol genes, and optionally the rev gene.

13. A process for producing retroviruses, the process comprising the steps:

(a) introducing a retroviral Transfer Vector comprising 5' and 3' retrovirus LTRs, a retrovirus packaging signal and a retroviral rev gene into a retroviral packaging cell as claimed in claim 9, wherein the retroviral packaging cell comprises retroviral env and gag-pol genes stably integrated into its genome;

(b) culturing the cell under conditions such that retroviruses are assembled and secreted by the cell; and (c) harvesting packaged retrovirus from supernatant.

14. A process for producing retroviruses, the process comprising the steps:

(a) introducing a retroviral Transfer Vector comprising a transgene into a retroviral packaging cell as claimed in claim 9, wherein the retroviral packaging cell comprises retroviral env, gag-pol and rev genes stably integrated into its genome;

(b) culturing the cell under conditions such that retroviruses are assembled and secreted by the cell; and (c) harvesting packaged retrovirus from supernatant.

15. A mammalian cell comprising a double-stranded nucleic acid as claimed in claim 8, wherein the double-stranded nucleic acid is stably integrated into a nuclear genome of the mammalian cell.

16. The retroviral vector as claimed in claim 7, wherein the retroviral vector is a lentiviral vector.

* * * * *

SEQUENCE LISTING

<160> NUMBER OF SEQ ID NOS: 14

<210> SEQ ID NO 1
<211> LENGTH: 2571
<212> TYPE: DNA
<213> ORGANISM: Human immunodeficiency virus type 1

<400> SEQUENCE: 1

```
atgagagtga aggagaaata tcagcacttg tggagatggg ggtggagatg gggcaccatg      60
ctccttggga tgttgatgat ctgtagtgct acagaaaaat tgtgggtcac agtctattat     120
ggggtacctg tgtggaagga agcaaccacc actctatttt gtgcatcaga tgctaaagca     180
tatgatacag aggtacataa tgtttgggcc acacatgcct gtgtacccac agaccccaac     240
ccacaagaag tagtattggt aaatgtgaca gaaaatttta acatgtggaa aaatgacatg     300
gtagaacaga tgcatgagga taataatcagt ttatgggatc aaagcctaaa gccatgtgta     360
aaattaaccc cactctgtgt tagtttaaag tgcactgatt tgaagaatga tactaatacc     420
aatagtagta gcgggagaat gataatggag aaaggagaga taaaaaactg ctctttcaat     480
atcagcacaa gcataagagg taaggtgcag aaagaatatg cattttttta taaacttgat     540
ataataccaa tagataatga tactaccagc tataagttga caagttgtaa cacctcagtc     600
attacacagg cctgtccaaa ggtatccttt gagccaattc ccatacatta ttgtgccccg     660
gctggttttg cgattctaaa atgtaataat aagacgttca atggaacagg accatgtaca     720
aatgtcagca cagtacaatg tacacatgga attaggccag tagtatcaac tcaactgctg     780
ttaaatggca gtctagcaga agaagaggta gtaattagat ctgtcaattt cacggacaat     840
gctaaaacca ataatagtaca gctgaacaca tctgtagaaa ttaattgtac aagacccaac     900
aacaatacaa gaaaaagaat ccgtatccag agaggaccag ggagagcatt tgttacaata     960
ggaaaaatag gaaatatgag acaagcacat tgtaacatta gtagagcaaa atggaataac    1020
actttaaaac agatagctag caaattaaga gaacaatttg gaaataataa aacaataatc    1080
tttaagcaat cctcaggagg ggacccagaa attgtaacgc acagttttaa ttgtggaggg    1140
gaattttct actgtaattc aacacaactg tttaatagta cttggtttaa tagtacttgg    1200
agtactgaag ggtcaaataa cactgaagga agtgacacaa tcaccctccc atgcagaata    1260
aaacaaatta taaacatgtg gcagaaagta ggaaaagcaa tgtatgcccc tcccatcagt    1320
ggacaaatta gatgttcatc aaatattaca gggctgctat taacaagaga tggtggtaat    1380
agcaacaatg agtccgagat cttcagacct ggaggaggag atatgaggga caattggaga    1440
agtgaattat ataaatataa agtagtaaaa attgaaccat taggagtagc acccaccaag    1500
gcaaagagaa gagtggtgca gagagaaaaa agagcagtgg aataggagc tttgttcctt    1560
gggttcttgg gagcagcagg aagcactatg ggcgcagcct caatgacgct gacggtacag    1620
gccagacaat tattgtctgg tatagtgcag cagcagaaca tttgctgag gctattgag    1680
gcgcaacagc atctgttgca actcacagtc tggggcatca agcagctcca ggcaagaatc    1740
```

-continued

```
ctggctgtgg aaagatacct aaaggatcaa cagctcctgg ggatttgggg ttgctctgga    1800
aaactcattt gcaccactgc tgtgccttgg aatgctagtt ggagtaataa atctctggaa    1860
cagatttgga atcacacgac ctggatggag tgggacagag aaattaacaa ttacacaagc    1920
ttaatacact ccttaattga agaatcgcaa aaccagcaag aaaagaatga acaagaatta    1980
ttggaattag ataaatgggc aagtttgtgg aattggttta acataacaaa ttggctgtgg    2040
tatataaaat tattcataat gatagtagga ggcttggtag gtttaagaat agttttttgct   2100 gtactttcta tagtgaatag agttaggcag ggatattcac cattatcgtt tcagacccac    2160
ctcccaaccc cgaggggacc cgacaggccc gaaggaatag aagaagaagg tggagagaga    2220
gacagagaca gatccattcg attagtgaac ggatccttgg cacttatctg ggacgatctg    2280
cggagcctgt gcctcttcag ctaccaccgc ttgagagact tactcttgat tgtaacgagg    2340
attgtggaac ttctgggacg caggggggtgg gaagccctca aatattggtg gaatctccta   2400
cagtattgga gtcaggaact aaagaatagt gctgttagct tgctcaatgc cacagccata    2460
gcagtagctg aggggacaga tagggttata gaagtagtac aaggagcttg tagagctatt    2520
cgccacatac ctagaagaat aagacagggc ttggaaagga ttttgctata a             2571
```

<210> SEQ ID NO 2
<211> LENGTH: 856
<212> TYPE: PRT
<213> ORGANISM: Human immunodeficiency virus type 1

<400> SEQUENCE: 2

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
        50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
        130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220
```

-continued

```
Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
            245                 250                 255

Thr Gln Leu Leu Leu Asn Gly Ser Leu Ala Glu Glu Val Val Ile
        260                 265                 270

Arg Ser Val Asn Phe Thr Asp Asn Ala Lys Thr Ile Ile Val Gln Leu
    275                 280                 285

Asn Thr Ser Val Glu Ile Asn Cys Thr Arg Pro Asn Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
            325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
            405                 410                 415

Pro Cys Arg Ile Lys Gln Ile Ile Asn Met Trp Gln Lys Val Gly Lys
        420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
            485                 490                 495

Ala Pro Thr Lys Ala Lys Arg Arg Val Val Gln Arg Glu Lys Arg Ala
        500                 505                 510

Val Gly Ile Gly Ala Leu Phe Leu Gly Phe Leu Gly Ala Ala Gly Ser
    515                 520                 525

Thr Met Gly Ala Ala Ser Met Thr Leu Thr Val Gln Ala Arg Gln Leu
530                 535                 540

Leu Ser Gly Ile Val Gln Gln Asn Asn Leu Leu Arg Ala Ile Glu
545                 550                 555                 560

Ala Gln Gln His Leu Leu Gln Leu Thr Val Trp Gly Ile Lys Gln Leu
            565                 570                 575

Gln Ala Arg Ile Leu Ala Val Glu Arg Tyr Leu Lys Asp Gln Gln Leu
        580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
610                 615                 620

His Thr Thr Trp Met Glu Trp Asp Arg Glu Ile Asn Asn Tyr Thr Ser
625                 630                 635                 640
```

```
Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 3
<211> LENGTH: 1533
<212> TYPE: DNA
<213> ORGANISM: Vesicular stomatitis virus

<400> SEQUENCE: 3
atgaagtgtc tgctgtacct ggcgttcctg tttatcgggg tgaactgcaa gttcactatc      60
gtgtttccgc acaaccaaaa gggcaactgg aaaaacgtgc cttcaaatta ccattattgc     120
cccagcagct cggacctgaa ctggcacaat gacctcattg gaaccgcgct gcaggtgaag     180
atgccaaaga gccacaaggc tatccaggct gacggatgga tgtgccacgc gtcaaaatgg     240
gtgactacct gcgatttccg ctggtacgga ccaaaataca tcacgcacag catcagatca     300 ttcacccccgt cagtggaaca atgcaaagaa tccatcgaac agactaagca gggaacctgg     360
ctgaaccctg gatttccgcc gcagtcgtgt gggtacgcaa ccgtgaccga tgcagaggcc     420
gtgatcgtgc aagtcacgcc gcatcacgtg cttgtggacg agtacaccgg agaatgggtc     480
gattcccagt tcatcaacgg caagtgctcc aactacattt gcccaaccgt gcacaacagc     540
actacttggc acagcgacta caaagtgaag ggtctgtgtg attccaacct gatctccatg     600
gatatcactt tcttctcgga agacggcgaa ctgtcctcac tgggcaaaga aggaactggg     660
tttcgctcaa attcttcgc ctacgaaact ggaggaaaag cctgcaagat gcagtactgc     720
aagcactggg gcgtgagact acccagcggt gtctggttcg agatggccga taaggacctg     780
tttgcagcag cgagattccc ggaatgccct gagggatcga gcatctccgc tccaagccaa     840
acttcagtgg acgtgagcct gatccaggac gtggaacgga ttctcgacta ctcgctgtgc     900
```

```
caggagacct ggtcgaagat cagagcggga ctgcccatct caccggtgga cctgtcctac    960
ctggcgccaa agaatccggg cactggaccg gcgttcacca tcatcaacgg caccctcaaa   1020
tacttcgaga cgcggtacat ccgggtggac atcgcagctc cgatcctctc ccggatggtg   1080
ggaatgatct cggggactac taccgaacgc gagctctggg acgactgggc accttacgag   1140
gatgtcgaga tcggacctaa cggagtgctc cggacctcct ccgggtacaa gttccctctg   1200
tacatgatcg gccatggcat gctggactcg gatctgcatc tgtcgtccaa agcacaggtg   1260
tttgaacacc cacacattca agacgccgcc agccagctgc cggacgatga gtcgctgttc   1320
ttcggagaca cgggcttgtc aaagaatccc atcgagctgg tggaaggatg gttttcatcc   1380
tggaaaagca gcatcgcttc attcttcttc atcattggcc tgatcatcgg cctatttcta   1440
gtcctgcggg tgggaattca tctgtgcatc aagctcaagc acactaagaa gcggcaaatc   1500
tacactgata tcgagatgaa tcgcctgggc aag                                1533

<210> SEQ ID NO 4
<211> LENGTH: 511
<212> TYPE: PRT
<213> ORGANISM: Vesicular stomatitis virus

<400> SEQUENCE: 4

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255
```

```
Asp Lys Asp Leu Phe Ala Ala Ala Arg Phe Pro Glu Cys Pro Glu Gly
                260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
        290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Gly Asp Thr Gly Leu Ser Lys
        435                 440                 445

Asn Pro Ile Glu Leu Val Glu Gly Trp Phe Ser Ser Trp Lys Ser Ser
450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510

<210> SEQ ID NO 5
<211> LENGTH: 4307
<212> TYPE: DNA
<213> ORGANISM: Human immunodeficiency virus type 1

<400> SEQUENCE: 5
atgggtgcga gagcgtcagt attaagcggg ggagaattag atcgatggga aaaaattcgg      60
ttaaggccag ggggaaagaa aaaatataaa ttaaaacata tagtatgggc aagcagggag     120
ctagaacgat tcgcagttaa tcctggcctg ttagaaacat cagaaggctg tagacaaata     180
ctgggacagc tacaaccatc ccttcagaca ggatcagaag aacttagatc attatataat     240
acagtagcaa ccctctattg tgtgcatcaa aggatagaga taaaagacac caaggaagct     300
ttagacaaga tagaggaaga gcaaaacaaa agtaagaaaa agcacagca agcagcagct     360 gacacaggac acagcaatca ggtcagccaa aattacccta gtgtgcagaa catccagggg     420
caaatggtac atcaggccat atcacctaga actttaaatg catgggtaaa agtagtagaa     480
gagaaggctt tcagcccaga agtgataccc atgttttcag cattatcaga aggagccacc     540
ccacaagatt taaacaccat gctaaacaca gtggggggac atcaagcagc catgcaaatg     600
ttaaaagaga ccatcaatga ggaagctgca gaatgggata gagtgcatcc agtgcatgca     660
gggcctattg caccaggcca gatgagagaa ccaaggggaa gtgacatagc aggaactact     720
```

```
agtacccttc aggaacaaat aggatggatg acacataatc cacctatccc agtaggagaa      780
atctataaaa gatggataat cctgggatta aataaaatag taagaatgta tagccctacc      840
agcattctgg acataagaca aggaccaaag gaacccttta gagactatgt agaccgattc      900
tataaaactc taagagccga gcaagcttca caagaggtaa aaaattggat gacagaaacc      960
ttgttggtcc aaaatgcgaa cccagattgt aagactattt aaaagcatt gggaccagga     1020 gcgacactag aagaaatgat gacagcatgt cagggagtgg ggggacccgg ccataaagca     1080
agagttttgg ctgaagcaat gagccaagta acaaatccag ctaccataat gatacagaaa     1140
ggcaattttt ggaaccaaag aaagactgtt aagtgtttca attgtggcaa agaagggcac     1200
atagccaaaa attgcagggc ccctaggaaa aagggctgtt ggaaatgtgg aaaggaagga     1260
caccaaatga agattgtac tgagagacag gctaattttt tagggaagat ctggccttcc      1320
cacaagggaa ggccagggaa ttttcttcag agcagaccag agccaacagc cccaccagaa     1380
gagagcttca ggtttgggga agagacaaca actccctctc agaagcagga gccgatagac     1440
aaggaactgt atcctttagc ttccctcaga tcactctttg gcagcgaccc ctcgtcacaa     1500
taaagatagg ggggcaatta aaggaagctc tattagatac aggagcagat gatacagtat     1560
tagaagaaat gaatttgcca ggaagatgga accaaaaat gatagggga attggaggtt      1620 ttatcaaagt aagacagtat gatcagatac tcatagaaat ctgcggacat aaagctatag     1680
gtacagtatt agtaggacct acacctgtca acataattgg aagaaatctg ttgactcaga     1740
ttggctgcac tttaaatttt cccattagtc ctattgagac tgtaccagta aaattaaagc     1800
caggaatgga tggcccaaaa gttaaacaat ggccattgac agaagaaaaa ataaaagcat     1860
tagtagaaat ttgtacagaa atggaaaagg aaggaaaaat ttcaaaaatt gggcctgaaa     1920
atccatacaa tactccagta tttgccataa agaaaaaaga cagtactaaa tggagaaaat     1980
tagtagattt cagagaactt aataagagaa ctcaagattt ctgggaagtt caattaggaa     2040
taccacatcc tgcagggtta aaacagaaaa aatcagtaac agtactggat gtgggcgatg     2100
catatttttc agttccctta gataaagact tcaggaagta tactgcattt accataccta     2160
gtataaacaa tgagacacca gggattagat atcagtacaa tgtgcttcca cagggatgga     2220
aaggatcacc agcaatattc cagtgtagca tgacaaaaat cttagagcct tttagaaaac     2280
aaaatccaga catagtcatc tatcaataca tggatgattt gtatgtagga tctgacttag     2340
aaatagggca gcatagaaca aaaatagagg aactgagaca acatctgttg aggtggggat     2400
ttaccacacc agacaaaaaa catcagaaag aacctccatt cctttggatg ggttatgaac     2460
tccatcctga taaatggaca gtacagccta tagtgctgcc agaaaaggac agctggactg     2520
tcaatgacat acagaaatta gtgggaaaat tgaattgggc aagtcagatt tatgcaggga     2580
ttaaagtaag gcaattatgt aaacttctta ggggaaccaa agcactaaca gaagtagtac     2640
cactaacaga agaagcagag ctagaactgg cagaaaacag ggagattcta aaagaaccgg     2700
tacatggagt gtattatgac ccatcaaaag acttaatagc agaaatacag aagcaggggc     2760
aaggccaatg gacatatcaa atttatcaag agccatttaa aaatctgaaa acaggaaagt     2820
atgcaagaat gaagggtgcc cacactaatg atgtgaaaca attaacagag gcagtacaaa     2880
aaatagccac agaaagcata gtaatatggg gaaagactcc taaatttaaa ttacccatac     2940
aaaaggaaac atgggaagca tggtggacag agtattggca agccacctgg attcctgagt     3000
gggagtttgt caatacccct cccttagtga agttatggta ccagttagag aaagaaccca     3060
```

```
taataggagc agaaactttc tatgtagatg gggcagccaa tagggaaact aaattaggaa    3120
aagcaggata tgtaactgac agaggaagac aaaaagttgt cccctaacg acacaacaa     3180 atcagaagac tgagttacaa gcaattcatc tagctttgca ggattcggga ttagaagtaa    3240
acatagtgac agactcacaa tatgcattgg gaatcattca agcacaacca gataagagtg    3300
aatcagagtt agtcagtcaa ataatagagc agttaataaa aaaggaaaaa gtctacctgg    3360
catgggtacc agcacacaaa ggaattggag gaaatgaaca agtagataaa ttggtcagtg    3420
ctggaatcag gaaagtacta ttttagatg gaatagataa ggcccaagaa gaacatgaga     3480
aatatcacag taattggaga gcaatggcta gtgattttaa cctaccacct gtagtagcaa     3540
aagaaatagt agccagctgt gataaatgtc agctaaaagg ggaagccatg catggacaag    3600
tagactgtag cccaggaata tggcagctag attgtacaca tttagaagga aaagttatct    3660
tggtagcagt tcatgtagcc agtggatata tagaagcaga agtaattcca gcagagacag    3720
ggcaagaaac agcatacttc ctcttaaaat tagcaggaag atggccagta aaaacagtac    3780
atacagacaa tggcagcaat ttcaccagta ctacagttaa ggccgcctgt tggtgggcgg    3840
ggatcaagca ggaatttggc attccctaca atccccaaag tcaaggagta atagaatcta    3900
tgaataaaga attaagaaaa attataggac aggtaagaga tcaggctgaa catcttaaga    3960
cagcagtaca aatggcagta ttcatccaca attttaaaag aaaaggggg attgggggt      4020 acagtgcagg ggaagaata gtagacataa tagcaacaga catacaaact aaagaattac     4080
aaaaacaaat tacaaaaatt caaaattttc gggtttatta cagggacagc agagatccag    4140
tttggaaagg accagcaaag ctcctctgga aggtgaagg ggcagtagta atacaagata     4200
atagtgacat aaaagtagtg ccaagaagaa aagcaaagat catcagggat tatggaaaac    4260
agatggcagg tgatgattgt gtggcaagta gacaggatga ggattaa                  4307

<210> SEQ ID NO 6
<211> LENGTH: 348
<212> TYPE: DNA
<213> ORGANISM: Human immunodeficiency virus type 1

<400> SEQUENCE: 6
atggcaggcc gctcagggga ctcggatgag gatctgctga aggcggtgcg gctcatcaaa     60
ttcctgtacc agagcaaccc gccaccgaac cccgaaggaa ctcgccaggc tcgcaggaac    120
cgccgcagac gctggcgcga acggcagcgc cagatccaca gcatcagcga acgcatcctg    180
tcaacttact gggacggtc agcggaacct gtcccgctgc agctgccgcc gctggagcgc    240
ctgactctgg attgcaacga agactgcgga accagcggaa cccagggcgt gggaagccca    300
cagatcctgg tggaatcgcc taccatcttg gaaagcggcg cgaaagaa                 348

<210> SEQ ID NO 7
<211> LENGTH: 116
<212> TYPE: PRT
<213> ORGANISM: Human immunodeficiency virus type 1

<400> SEQUENCE: 7

Met Ala Gly Arg Ser Gly Asp Ser Asp Glu Asp Leu Leu Lys Ala Val
1               5                   10                  15

Arg Leu Ile Lys Phe Leu Tyr Gln Ser Asn Pro Pro Pro Asn Pro Glu
            20                  25                  30

Gly Thr Arg Gln Ala Arg Arg Asn Arg Arg Arg Arg Trp Arg Glu Arg
        35                  40                  45
```

```
Gln Arg Gln Ile His Ser Ile Ser Glu Arg Ile Leu Ser Thr Tyr Leu
 50                  55                  60

Gly Arg Ser Ala Glu Pro Val Pro Leu Gln Leu Pro Pro Leu Glu Arg
 65                  70                  75                  80

Leu Thr Leu Asp Cys Asn Glu Asp Cys Gly Thr Ser Gly Thr Gln Gly
                 85                  90                  95

Val Gly Ser Pro Gln Ile Leu Val Glu Ser Pro Thr Ile Leu Glu Ser
            100                 105                 110

Gly Ala Lys Glu
        115

<210> SEQ ID NO 8
<211> LENGTH: 19
<212> TYPE: DNA
<213> ORGANISM: Escherichia coli

<400> SEQUENCE: 8
tccctatcag tgatagaga                                                  19

<210> SEQ ID NO 9
<211> LENGTH: 624
<212> TYPE: DNA
<213> ORGANISM: Escherichia coli

<400> SEQUENCE: 9
atgtcgcgcc tggacaaaag caaagtgatt aactcagcgc tggaactgtt gaatgaggtg      60
ggaattgaag gactcactac tcgcaagctg gcacagaagc tgggcgtcga gcagccaacg     120
ctgtactggc atgtgaagaa taacgggcg ctcctagacg cgcttgccat cgaaatgctg      180
gaccgccatc acacccactt ttgcccctg gagggcgaat cctggcaaga ttttctgcgg      240
aacaatgcaa agtcgttccg gtgcgctctg ctgtcccacc gcgatggcgc aaaagtgcac     300
ctgggcactc ggcccaccga gaaacaatac gaaaccctgg aaaaccaact ggctttcctt     360
tgccaacagg gattttcact ggagaatgcc ctgtacgcac tatccgcggt cggccacttt     420
accctgggat gcgtcctcga agatcaggag caccaagtcg ccaaggagga agagaaaact     480
cctaccactg actcaatgcc tccgctcctg agacaagcca tcgagctgtt cgaccaccag     540
ggtgctgaac ctgcatttct gttcgggctt gaactgatta tctgcggcct ggagaaacag     600
ttgaagtgcg agtcgggatc ctag                                           624

<210> SEQ ID NO 10
<211> LENGTH: 207
<212> TYPE: PRT
<213> ORGANISM: Escherichia coli

<400> SEQUENCE: 10

Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
             20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
     50                  55                  60

Thr His Phe Cys Pro Leu Glu Gly Glu Ser Trp Gln Asp Phe Leu Arg
 65                  70                  75                  80
```

-continued

```
Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205
```

<210> SEQ ID NO 11
<211> LENGTH: 876
<212> TYPE: DNA
<213> ORGANISM: Baculovirus

<400> SEQUENCE: 11

```
atgaacgagg acactccgcc gttttatttt atcaatacgc gcgacaactt tcgcgataac     60
atcgccgaac acgtattcga tatgttacta gaaagacatg gctcgtttga aaattatccc    120
attgtaaaca cggcattcat caacagcttg atcgttaacg ggtttaaata caatcaagtc    180
gatgaccacg ttgtgtgcga gtattgtgaa gcagaaataa aaaattggtc cgaagacgag    240
tgtattgaat atgcacacgt aaccttgtcg ccgtattgcg cctacgccaa taagattgct    300
gagcatgaat cgtttggcga caacattacc atcaacgctg tactggtaaa agaaggcaga    360
cccaagtgtg tgtacagatg catgtccaat ttacagtcgc gtatggatac gtttgttact    420
ttttggcctg ccgcattgcg tgacatgatt ataaacatcg cggaagcggg actttttttac    480 acgggtcgcg gagacgaaac tgtatgtttc ttttgcgatt gttgcgtacg tgattggcat    540
actaacgaag acgcctggca gcgacacgcc accgaaaacc cgcaatgcta ctttgtgctg    600
tcggtgaaag gtaaagaatt ttgtcaaaac gcaattactg ccactcacgt tgataaacgt    660
gacgatgacg acgacgacga tgataattta aacgagagcg tcgatgacat tgaggaaaaa    720
tacgaatgca aagtctgtct tgaacgccaa cgcgacgcag tgcttatgcc ttgtcggcat    780
ttttgtgttt gcgttcagtg ttattttggt ttagatcaaa agtgtccgac ctgtcgtcaa    840
gacgtcaccg atttcataaa aatatttgtg gtgtag                              876
```

<210> SEQ ID NO 12
<211> LENGTH: 1521
<212> TYPE: DNA
<213> ORGANISM: Epstein Barr virus

<400> SEQUENCE: 12

```
atgggagatc gtagcgaagt ccccggtccg gcacgccccg gacctccggg aattggcccc     60
gaaggccctc taggacagct cctgcgtcgg caccgcagtc cctccccgac ccgtggaggc    120
caagagcccc ggcgggtcag acgccgcgta ttagtccagc aggaagagga agtagtaagt    180
ggctcaccat cagggccccg gggagacagg tcagaggtcc caggcccagc ccgccctggc    240
```

```
ccgccgggta tcggacccga agggcccctg ggccagctgt tgcgccggca cagatcaccc      300
agccccaccc gcggcggtca ggaacctcgc cgggtcagac ggcgggtgct cgtacaacag      360
gaagaggaag ttgtttctgg atcgccctcg ggcccgcgcg gcgaccgctc agaggtgcct      420
ggaccagccc ggcctgggcc cccggaatc ggacctgaag gaccgctggg tcagttacta      480
cgccggcacc ggtccccttc gccgactcgg ggcgggcagg aaccccggcg cgtgaggcgt      540
cgcgtcctgg tccagcagga ggaagaggtt gtcagcggca gcccatccgg gccgaggggg      600
gatcgttcgg aagtgcccgg cccagcacgc ccgggcccgc caggtattgg gcccgaaggt      660
ccgttaggtc agctgctccg gcggcatagg tcaccatccc cgactcgggg cggccaggaa      720
ccgcggagag tgcgccggag agtgctggtg caacaggagg aagaagtcgt gtccgggtcg      780
ccgtcaggtc ctcggggcga ccggtcagaa gtacctggac cggcccgccc ggaccgccg      840 ggcatcgggc cggaaggccc cctgggacag ctgctgcgga gacatagatc gccatccccc      900 accgagaggcg acaggaacc cgccgcgtg cgccgcggg tgctggttca gcaagaagaa      960
gaggttgtgt cgggttcacc tagcggcccg agaggcgacc ggagcgaagt gccaggacca     1020
gcacgtccgg gccctccagg tatcggccca aaggaccac tgggacaact gctgagacgc     1080
catcgctcgc cgagccctac gcgcggaggt caagaaccga gacgggtccg cagacgagtc     1140
ctcgttcaac aagaagaaga ggtcgtgtct ggaagcccgt ctggcccaag aggggacaga     1200
agcgaggtgc cgggaccggc gcggccgggg ccgccgggga tcgggcctga aggtccgctg     1260
gggcagctct tgcgcagaca ccgctcgccc agcccaaccc gcggtggaca agaaccccga     1320
cgggtgcggc ggcgcgtgct cgtgcaacaa gaagaagagg ttgtctcggg ctcgccatct     1380
ggcccgctca gaccaagacc gcgaccgccg gcccggtccc tccgcgaatg gctgctgcgc     1440
atcagagaca gattcgagcc gccaactgaa accacccagc ggcagtccat ctacattgag     1500
gaagaggaag atgaggatta g                                              1521

<210> SEQ ID NO 13
<211> LENGTH: 702
<212> TYPE: DNA
<213> ORGANISM: Homo sapiens

<400> SEQUENCE: 13
atgagccagt caaatcggga actggtggtg gattttctga gctacaagct ctcgcaaaag       60
ggctactcat ggagccagtt ttcggatgtc gaagaaaacc ggaccgaggc tccagagggc      120
accgaatcgg agatggaaac tccgtcagca atcaacggaa atccatcatg gcacctggca      180
gatagcccgg cggtgaacgg agcaaccgga cattcaagct ccctggacgc cagagaagtg      240
attccgatgg cggcagtgaa gcaggcgcta cgcgaagcgg gagacgagtt cgagctgcgg      300
tacaggagag cttttagcga cctgactagc cagctccaca tcactccggg gaccgcctac      360
cagtcgtttg aacaggtggt gaacgagctg tttcgggatg gagtcaactg ggcagaatc      420 gtggccttct tttccttcgg cggtgcgctg tgcgtcgaat ccgtgacaa ggagatgcag      480 gtcctggtca gccggatcgc agcgtggatg ccacttatc tcaacgatca cctggagccg      540
tggattcaag agaatggggg ctgggacacc ttcgtgaac tgtatggaaa caacgcggca      600
gcagagtcga ggaagggcca agaacgcttt aatcggtggt tcctgactgg aatgacggtg      660
gcaggagtgg tgctactggg ctcgcttttc agccgcaaat aa                        702

<210> SEQ ID NO 14
<211> LENGTH: 16
```

-continued

```
<212> TYPE: PRT
<213> ORGANISM: Vesicular stomatitis virus

<400> SEQUENCE: 14

Met Leu Ser Tyr Leu Ile Phe Ala Leu Ala Val Ser Pro Ile Leu Gly
1               5                   10                  15
```